(12) United States Patent
Mizuno

(10) Patent No.: US 7,462,484 B2
(45) Date of Patent: Dec. 9, 2008

(54) AMORPHOUS CELL DELIVERY VEHICLE TREATED WITH PHYSICAL/PHYSICOCHEMICAL STIMULI

(75) Inventor: Shuichi Mizuno, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 207 days.

(21) Appl. No.: 11/194,040

(22) Filed: Jul. 29, 2005

(65) Prior Publication Data

US 2006/0034808 A1 Feb. 16, 2006

Related U.S. Application Data

(60) Provisional application No. 60/592,786, filed on Jul. 30, 2004.

(51) Int. Cl.
*C12N 5/00* (2006.01)
*C12N 5/02* (2006.01)

(52) U.S. Cl. .................. 435/372; 435/373
(58) Field of Classification Search ............... 435/372, 435/373
See application file for complete search history.

(56) References Cited

U.S. PATENT DOCUMENTS

| 4,846,835 A | 7/1989 | Grande |
| 6,171,610 B1 | 1/2001 | Vacanti et al. |
| 6,242,247 B1 | 6/2001 | Mainil-Varlet et al. |
| 6,432,713 B2 | 8/2002 | Takagi et al. |
| 2001/0014473 A1* | 8/2001 | Rieser et al. ............. 435/297.1 |
| 2003/0138873 A1 | 7/2003 | Masuda et al. |
| 2004/0013712 A1 | 1/2004 | Parma |

OTHER PUBLICATIONS

Mizuno et al., J Cellular Physiology, 2002, 193:319-327.*
Bachrach N.M. et al., Changes in proteoglycan synthesis of chondrocytes in articular cartilage are associated with the time-dependent changes in their mechanical environment. J. Biomech. Dec. 1995;28(12):1561-9.
Bachrach N.M. et al., Incompressibility of the solid matrix of articular cartilage under high hydrostatic pressures. J. Biomech. May 1998;31(5):445-51.
Bryant S.J. et al., Controlling the spatial distribution of ECM components in degradable PEG hydrogels for tissue engineering cartilage. J. Biomed Mater Res A. Jan. 1, 2003;64(1):70-9.
Bryant S.J. et al., Hydrogel properties influence ECM production by chondrocytes photoencapsulated in poly(ethylene glycol) hydrogels. J Biomed Mater Res. Jan. 2002;59(1):63-72.
Buschmann M.D. et al., Altered aggrecan synthesis correlates with cell and nucleus structure in statically compressed cartilage. J. Cell Sci. Feb. 1996;109 ( Pt 2):499-508.
Buschmann M.D. et al., Mechanical compression modulates matrix biosynthesis in chondrocyte/agarose culture. J. Cell Sci. Apr. 1995;108 ( Pt 4):1497-508.

Comper W.D. et al., Non-electrostatic factor govern the hydrodynamic properties of articular cartilage proteoglycan. Biochem J. Jan. 15, 1993;289 ( Pt 2):543-7.
Darling EM et al., Articualr cartilage bioreactors and bioprocesses. Tissue Eng. Feb. 2003;9(1):9-26.
Demarteau O et al., Development and validation of a bioreactor for physical stimulation of engineered cartilage. Biorheology. 2003;40(1-3):331-6.
Gray M. et al., Mechanical and physiochemical determinants of the chondrocyte biosynthetic response. J Orthop Res. 1988;6(6):777-92.
Grogan SP et al., A static, closed and scaffold-free bioreactor system that permits chondrogenesis in vitro. Osteoarthritis Cartilage. Jun. 2003;11(6):403-11.
Guilak F. et al., Chondrocyte deformation and local tissue strain in articular cartilage: A confocal microscopy study. J Orthop Res. May 1995; 13(3):410-21.
Guilak F., The deformation behavior and viscoelastic properties of chondrocytes in articular cartilage. Biorheology. 2000;37(1-2):27-44.
Hall A. et al., The effects of hydrostatic pressure on matrix synthesis in articular cartilage. J Orthop Res. Jan. 1991;9(1):1-10.
Kim Y. et al., Mechanical regulation of cartilage biosynthetic behavior: physical stimuli. Arch Biochem Biophys. May 15, 1994;311(1):1-12.
Kim Y.J. et al., The role of cartilage streaming potential, fluid flow and pressure in the stimulation of chondrocyte biosynthesis during dynamic compression. J Biomech. Sep 1995;28(9):1055-66.
Klein-Nulend J. et al., Influence of intermittent compressive force on proteoglycan content in calcifying growth plate cartilage in vitro. J Biol Chem. Nov. 15, 1987;262(32):15490-5.
Lammi M.J. et al., Expression of reduced amounts of structurally altered aggrecan in articular cartilage chondrocytes exposed to high hydrostatic pressure. Biochem J. Dec. 15, 1994; 304 (Pt 3):723-30.
Mainil-Varlet P et al., Articalr cartilage repair using a tissue-engineered cartilage-like implant: an animal study. Osteoarthritis Cartilage. 2001;9 Suppl A:S6-15.
Mankin K.P. et al., Response of physeal cartilage to low-level compression and tension in organ culture. J Pediatr Orthop. Mar.-Apr. 1998;18(2):145-8.
Maroudas A., Biophysical chemistry of cartilaginous tissues with special reference to solute and fluid transport. Biorheology. Jun. 1975;12(3-4):233-48.
Martens PJ et al., Tailoring the degradation of hydrogels formed from multivinyl poly(ethylene glycol) and poly(vinyl alcohol) macromers for cartilage tissue engineering. Biomacromolecules. Mar.-Apr. 2003;4(2):283-92.

(Continued)

*Primary Examiner*—Ruth A Davis
(74) *Attorney, Agent, or Firm*—Wolf, Greenfield & Sacks, LLP

(57) ABSTRACT

Provided are compositions and methods for in vitro generation and in vivo use of tissue for the repair of defective tissue, especially cartilage. Chondrocytes or other cells are cultured in vitro in a biodegradable amorphous carrier within the confines of a space bounded by a semi-permeable membrane with a molecular weight cut-off of greater than 100 kDa. The culture can be subjected to physical/physicochemical conditions that mimic in vivo conditions of the tissue in need of repair or replacement. In one embodiment the invention provides an amorphous preparation of chondrocytes and their extracellular products, suitable for injection.

14 Claims, 6 Drawing Sheets

OTHER PUBLICATIONS

Mizuno S. et al., Chondroinduction of human dermal fibroblasts by demineralized bone in three-dimensional culture. Exp Cell Res. Aug. 25, 1996;227(1):89-97.

Mizuno S. et al., Effects of physical stimulation of chondrogenesis in vitro. Mat. Sci. Eng. C. Sep. 3, 1998,6:301-6.

Mow V.C. et al., The extracellular matrix, interstitial fluid and ions as a mechanical signal transducer in articular cartilage. Osteoarthritis Cartilage. Jan. 1999;7(1):41-58.

Mueller S.M. et al., Medium perfusion enhances osteogenesis by murine osteosarcoma cells in three-dimensional collagen sponges. J Bone Miner Res. Dec. 1999;14(12):2118-26.

O'Hara B.P. et al., Influence of cyclic loading on the nutrition of articular cartilage. Ann Rheum Dis. Jul. 1990;49(7):536-9.

Ostendorf R.H. et al., Intermittent loading induces the expression of 3-B-3(-) epitope in cultured bovine articular cartilage. J Rheumatol. Feb. 1994;21(2):287-92.

Palmoski M.J. et al., Effects of static and cyclic compressive loading on articular cartilage plugs in vitro. Arthritis Rheum. Jun. 1984;27(6):675-81.

Parkkinen et al., Effects of cyclic hydrostatic pressure on proteoglycan synthesis in cultured chondrocytes and articular cartilage explants. Arch Biochem Biophys. Jan. 1993;300(1):458-65.

Potter K et al., Cartilage formation in a hollow fiber bioreactor studied by proton magnetic resonance microscopy. Matrix Biol. Nov. 1998;17(7):513-23.

Sah R.L. et al., Biosynthetic response of cartilage explants to dynamic compression. J Orthop Res. 1989;7(5):619-36.

Saini S et al., Concentric cylinder bioreactor for production of tissue engineered cartilage: effect of seeding density and hydrodynamic loading on construct development. Biotechnol Prog. Mar.-Apr. 2003;19(2):510-21.

Torzilli P.A. et al., Characterization of cartilage metabolic response to static and dynamic stress using a mechanical explant test system. J Biomech. Jan. 1997;30(1):1-9.

\* cited by examiner

STIMULI
Static culture 7days

TB

Collagen Type 2

Constant hydrostatic pressure culture 7days

TB

Collagen Type 2

Cyclic hydrostatic pressure culture 7days

TB

Collagen Type 2

AMORPHOUS CELL DELIVERY VEHICLE TREATED WITH PHYSICAL/PHYSICOCHEMICAL STIMULI

RELATED APPLICATION

This application claims benefit under 35 U.S.C. 119(e) of U.S. Provisional Patent Application Ser. No. 60/592,786, filed Jul. 30, 2004, the entire content of which is incorporated herein by reference.

FIELD OF THE INVENTION

The invention is in the field of functional tissue engineering. More particularly, the invention in some aspects involves in vitro culture methods and products thereof, useful for regenerating tissue suitable for use in replacement or repair sites of damaged tissue.

BACKGROUND OF THE INVENTION

There are various methods for restoring a damaged tissue or a pathogenic part of a living body. One method is to substitute the damaged tissue or pathogenic part with materials other than a living tissue, such as plastic, metal, and/or ceramic to restore the damaged tissue or the pathogenic part. Another method is to substitute the damaged tissue or pathogenic part with parts from other individuals or other animals, or from a different location of the living body, for example, skin. These methods can have certain drawbacks, including physical wear and dislodgement of non-living tissues and availability or suitability of living tissue for certain purposes. A third method is to generate a new vital tissue in vitro.

Accordingly, a method of restoring a damaged tissue or a pathogenic part of a living body is to substitute the damaged part of a tissue by a tissue that is obtained by cultivating a cell or tissue in vitro. It has recently been reported that such method is generally possible as may be applicable to many tissues such as skin, cartilage, bone, blood vessels, liver, and pancreas. If a cell or tissue derived from a living body is cultivated outside the living body of a patient, and the cell or tissue obtained by the culture is applied to the restoration of a damaged part, a tissue can be regenerated in the body. Further, if the tissue applied to the restoration is derived from the individual that is to receive the cultivated tissue, there is no concern of immunological rejection of the tissue upon its implantation into the individual.

Articular cartilage coating the ends of flexibly joined bones takes over the function of the load distribution in the loaded joint. For this function the cartilage tissue is capable of reversibly taking up water under conditions of low load or pressure and then releasing water under conditions of increased load or pressure. Furthermore, the cartilage surfaces serve as sliding surfaces in the joints.

Cartilage is not vascularized and its ability to regenerate in vivo is very limited, particularly in adult individuals and if the piece of cartilage to be regenerated exceeds even a small volume. However, articular cartilage often suffers degeneration due to wear, age, disease, or traumatic or overuse injuries, involving a significantly greater volume than might be naturally regenerated. This kind of defect of the cartilage layer makes movement and loading of the affected joint painful and can lead to further complications such as inflammation, which can contribute to further damage to the cartilage layer.

For these reasons efforts have been made for quite some time to replace or repair missing or damaged cartilage, especially articular cartilage.

Methods to repair defects involving articular cartilage alone or articular cartilage and the subchondral bone tissue beneath it by milling or drilling the defect location to form a bore of an as precise geometry as possible, extracting a disk of cartilage or cartilage and bone of the same geometry from a less weight bearing location of, e.g., the same joint by means of boring or punching, and inserting this column into the bore at the site of the defect to be treated. In the same manner, larger defects with several bores are repaired (mosaic plasty).

A number of methods have been developed in an attempt to produce cartilage at least partly in vitro, i.e., to produce cartilage using vital natural cells under artificial conditions. A problem encountered in these methods is the fact that chondrocytes in these in vitro conditions have the tendency to de-differentiate into fibroblasts relatively rapidly. By the de-differentiation the chondrocytes lose, inter alia, the ability to produce type II collagen which is one of the most important components of cartilage tissue. Attempts to address the problem of de-differentiation of chondrocytes in vitro have included immobilizing the chondrocytes in highly cell-dense cultures in a monolayer or in a three-dimensional scaffold. Under these conditions, chondrocytes reproduce themselves without substantial de-differentiation, and they form an extracellular matrix which is at least similar to the extracellular matrix of native cartilage. A three-dimensional scaffold is used not only for immobilizing the cells but also for imparting mechanical stability after implantation which is needed because none of the cartilage tissues produced in the above manner has a stability which can withstand even a low mechanical strain.

SUMMARY OF THE INVENTION

A major goal of functional tissue engineering is development of neo-tissue (cell construct) to repair or replace damaged tissue. For orthopedic applications, rigidity and stiffness are critical for replacement of damaged tissue, since the implant must withstand weight-bearing, joint-loading, and stretching. The present invention is directed to a new system that addresses these issues with three main components: a degradable carrier, a semipermeable membrane, and a bioreactor that, inter alia, applies hydrostatic fluid pressure to the cells in culture.

The invention in certain aspects provides an in vitro method of generating new tissue for use in a subject by producing a liquid hydrogel-cell composition, which contains a biodegradable hydrogel and tissue precursor cells, in a cell culture space bounded at least in part by a semi-permeable membrane and cultured under physical/physicochemical conditions that mimic those of the tissue as it occurs in vivo. The semi-permeable membrane is selected so as to retain cells, any high molecular weight extracellular matrix elaborated by the cells, and high molecular weight degradation products of the biodegradable hydrogel carrier within the cell culture space. A feature in certain aspects of the invention is the use of an amorphous hydrogel or other biodegradable carrier, without a preformed scaffold or other support structure, such that the product of the in vitro culture is deformable to adopt a three-dimensional shape defined by a space or receptacle into which the product may be introduced, either in vitro or in vivo. The in vitro cell culture product can be implanted into a subject, for example by using a syringe or catheter. The methods and compositions of the invention are useful in the treatment of various tissues including, e.g., cartilaginous tissue.

The invention in certain aspects also features methods and compositions related to the generation and use of injectable cell/matrix compositions that include chondrogenic cells with endogenous extracellular matrix (ECM). The ECM generated using the in vitro culture methods of the invention advantageously closely emulates naturally occurring ECM in its biochemical, histological, and/or biomechanical characteristics.

In one aspect the invention provides a method of culturing cells in vitro. The method according to this aspect of the invention includes the steps of contacting a population of cells selected for in vitro culture with a biodegradable amorphous carrier; placing the contacted population of cells in a cell space for receiving the cells, said cell space being bounded at least in part by a semi-permeable membrane having a molecular weight cut-off greater than 100 kDa and up to 1,000 kDa; and periodically applying pressure to the contacted population of cells.

In one embodiment according to this aspect of the invention, the cells comprise chondrocytes and, optionally, precursor cells thereof.

In one embodiment according to this aspect of the invention, the cells consist essentially of chondrocytes.

In one embodiment according to this aspect of the invention, the biodegradable amorphous carrier comprises type I collagen.

In one embodiment according to this aspect of the invention, the biodegradable amorphous carrier comprises dextran beads.

In one embodiment according to this aspect of the invention, the biodegradable amorphous carrier comprises a hydrogel chosen from dextran, chondroitin sulfate, polyethylene glycol, hyaluronan, and any combination thereof.

In one embodiment according to this aspect of the invention, the cell space for receiving the cells consists of a semi-permeable membrane tube comprising at least one closable opening for receiving the cells.

In one embodiment according to this aspect of the invention, the cell space for receiving the cells consists of a semi-permeable membrane pouch comprising a closable opening for receiving the cells.

In one embodiment according to this aspect of the invention, the semi-permeable membrane has a molecular weight cut-off of at least 200 kDa.

In one embodiment according to this aspect of the invention, the semi-permeable membrane has a molecular weight cut-off of at least 250 kDa.

In one embodiment according to this aspect of the invention, the semi-permeable membrane has a molecular weight cut-off of at least 500 kDa.

In one embodiment according to this aspect of the invention, the semi-permeable membrane has a molecular weight cut-off of 1,000 kDa.

In one embodiment according to this aspect of the invention, the semi-permeable membrane is a semi-permeable membrane carrying a net positive charge.

In one embodiment according to this aspect of the invention, the semi-permeable membrane carrying the net positive charge is a semi-permeable membrane coated with poly-L-lysine.

In one embodiment according to this aspect of the invention, the periodically applying pressure comprises applying 0.5 to 3.5 MPa at 0.001 to 1 Hz.

In one aspect the invention provides a composition that includes an in vitro-expanded population of cells in contact with a biodegradable amorphous carrier.

In one embodiment according to this aspect of the invention, the cells comprise chondrocytes and, optionally, precursor cells thereof. The cell/matrix composition in this instance is termed a chondrocytic cell/matrix composition for purposes of this invention.

In one embodiment according to this aspect of the invention, the cells consist essentially of chondrocytes. The cell/matrix composition in this instance is also termed a chondrocytic cell/matrix composition for purposes of this invention.

In one embodiment according to this aspect of the invention, the biodegradable amorphous carrier comprises type I collagen.

In one embodiment according to this aspect of the invention, the biodegradable amorphous carrier comprises dextran beads.

In one embodiment according to this aspect of the invention, the biodegradable amorphous carrier comprises a hydrogel chosen from dextran, chondroitin sulfate, polyethylene glycol, hyaluronan, and any combination thereof.

In one embodiment according to this aspect of the invention, the cells and carrier are contained in a cell space for receiving the cells, said cell space being bounded at least in part by a semi-permeable membrane having a molecular weight cut-off greater than 100 kDa and up to 1,000 kDa.

In one embodiment according to this aspect of the invention, the semi-permeable membrane has a molecular weight cut-off of at least 200 kDa.

In one embodiment according to this aspect of the invention, the semi-permeable membrane has a molecular weight cut-off of at least 250 kDa.

In one embodiment according to this aspect of the invention, the semi-permeable membrane has a molecular weight cut-off of at least 500 kDa.

In one embodiment according to this aspect of the invention, the semi-permeable membrane has a molecular weight cut-off of 1,000 kDa.

In one aspect the invention provides a composition that includes a cell/matrix composition produced according to the method of culturing cells in vitro described above.

In one embodiment according to this aspect of the invention, the cell/matrix composition comprises chondrocytes and, optionally, precursor cells thereof. The cell/matrix composition in this instance is termed a chondrocytic cell/matrix composition for purposes of this invention.

In one embodiment according to this aspect of the invention, cells of the cell/matrix composition consist essentially of chondrocytes. The cell/matrix composition in this instance is also termed a chondrocytic cell/matrix composition for purposes of this invention.

In one embodiment according to this aspect of the invention, the cell/matrix composition comprises a biodegradable amorphous carrier comprising type I collagen.

In one embodiment according to this aspect of the invention, the cell/matrix composition comprises a biodegradable amorphous carrier comprising dextran beads.

In one embodiment according to this aspect of the invention, the cell/matrix composition comprises a biodegradable amorphous carrier comprising a hydrogel chosen from dextran, chondroitin sulfate, polyethylene glycol, hyaluronan, and any combination thereof.

In one embodiment according to this aspect of the invention, the cell/matrix composition is contained in a cell space for receiving the cells, said cell space being bounded at least in part by a semi-permeable membrane having a molecular weight cut-off greater than 100 kDa and up to 1,000 kDa.

In one embodiment according to this aspect of the invention, the semi-permeable membrane has a molecular weight cut-off of at least 200 kDa.

In one embodiment according to this aspect of the invention, the semi-permeable membrane has a molecular weight cut-off of at least 250 kDa.

In one embodiment according to this aspect of the invention, the semi-permeable membrane has a molecular weight cut-off of at least 500 kDa.

In one embodiment according to this aspect of the invention, the semi-permeable membrane has a molecular weight cut-off of 1,000 kDa.

In one aspect the invention provides a method of treating a damaged cartilaginous tissue. The method according to this aspect of the invention includes the step of introducing an effective amount of a chondrocytic cell/matrix composition of the invention into a site of damaged cartilaginous tissue to treat the damaged cartilaginous tissue.

In one embodiment according to this aspect of the invention, the cartilaginous tissue is an intervertebral disc.

In one aspect the invention provides a method of treating a damaged articular cartilage surface. The method according to this aspect of the invention includes the step of introducing an effective amount of a chondrocytic cell/matrix composition of the invention into a space defined by a surface layer or superficial transitional zone of cartilage overlying a site of damaged articular cartilage surface and cartilage or subchondral bone beneath the site of damaged articular cartilage surface, to treat the damaged articular cartilage surface.

In one embodiment according to this aspect of the invention, the introducing is performed as part of an arthroscopic procedure to treat the damaged articular cartilage surface.

In one embodiment according to this aspect of the invention, the damaged articular cartilage surface is a damaged articular cartilage surface of a knee.

In one embodiment according to this aspect of the invention, the damaged articular cartilage surface is a damaged articular cartilage surface of a hip.

In one embodiment according to this aspect of the invention, the damaged articular cartilage surface is a damaged articular cartilage surface of a joint chosen from shoulder, elbow, hand (intercarpal, carpometacarpal, intermetacarpal, metacarpophalangeal, interphalangeal), and temporomandibular.

In one aspect the invention provides a method of treating osteoarthritis in a subject. The method according to this aspect of the invention includes the step of introducing, in a subject having osteoarthritis of a joint, an effective amount of a chondrocytic cell/matrix composition of the invention into a space defined by a surface zone cartilage overlying a site of damaged articular cartilage surface and subchondral bone beneath the site of damaged articular cartilage surface of the joint, to treat the osteoarthritis.

These and other aspects and embodiments of the invention will be described in further detail in connection with the detailed description of the invention.

BRIEF DESCRIPTION OF THE DRAWINGS

The figures are illustrative only and are not required for enablement of the inventions disclosed herein.

DETAILED DESCRIPTION OF THE INVENTION

Figure 1:
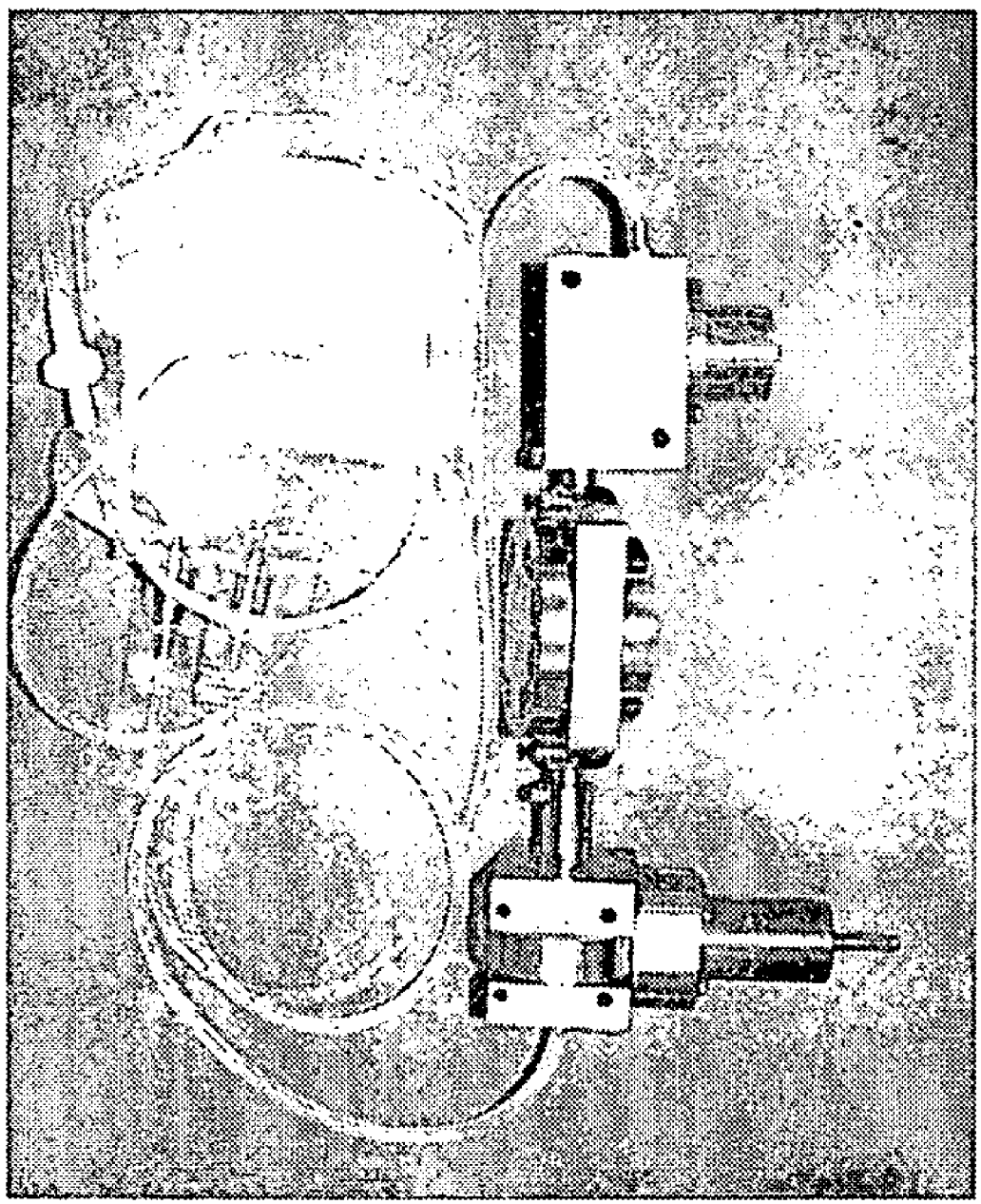
FIG. 1 is a photographic image depicting a hydrostatic pressure/perfusion culture system (bioreactor) designed for delivery of positive hydrostatic fluid pressure to culture sponges with or without constant perfusion of medium. The basic system includes (1) a medium reservoir with gas exchange silicon tubing, (2) a perfusion pump (a single-piston cylinder pump), (3) a culture chamber, and (4) a back-pressure control module. The cells with semi-permeable membrane pouch are suspended in the chamber, which is maintained at a specified temperature, e.g., 37° C. The magnitude of hydrostatic fluid pressure, perfusion rate, $O_2/CO_2$ gas concentration, and temperature are set and controlled using a computer.

The invention provides methods of, and compositions for, growing new tissue such as, for example, cartilage, as well as methods of use of said new tissue compositions for treatment of damaged tissue in a subject.

1. Definitions

Unless otherwise defined, all technical and scientific terms used herein have the same meaning as commonly understood by one of ordinary skill in the art to which this invention belongs.

As used herein, a population of cells selected for in vitro culture refers to any suitable collection of living cells isolated from their natural environment and provided for in vitro culture. The population of cells can be essentially homogeneous in terms of cell type, or it can be heterogeneous. For example, in one embodiment a homogeneous population of cells can include a representative sample of cells derived from an established cell line, a clone of cells, a source of adult stem cells, or an outgrowth of a primary culture. In one embodiment a heterogeneous population of cells can include two or more cell types and can originate from any suitable source or sources including representative samples of cells derived from one or more established cell lines, clones of cells, primary cultures, and any combination thereof. In one embodiment the population of cells is a collection of cells obtained from a source of hyaline (e.g., articular) cartilage. Such a population can include, without limitation, chondrocytes, fibroblastic cells, dermal fibroblasts, and synovial membrane cells. In one embodiment the population of cells consists essentially of chondrocytes. In one embodiment the population of cells includes precursor cells of chondrocytes. In one embodiment the population of cells includes representing dedifferentiated chondrocytes.

As used herein, a biodegradable amorphous carrier refers to any suitable hydrogel lacking a predetermined three-dimensional shape of its own at room temperature to physiologic temperature (i.e., 20-38° C.) and which degrades to an appreciable extent over a period of two weeks to about six weeks under sterile conditions that are suitable for in vitro culture of mammalian cells. Such conditions include temperature, pH, salt, and the presence of enzymes or tissue culture medium components, supplements, or waste products which may act on the hydrogel, either directly or indirectly, to reduce its molecular weight. Degradation can be assessed in terms of mean molecular weight, such that, for example, a carrier that is half degraded can refer to a carrier that has a mean molecular weight that is 50 percent of its initial mean molecular weight. Alternatively and equivalently, a carrier that is half degraded can refer to a carrier that has only 50 percent of its starting amount of initial mean molecular weight material. Methods for determining mean molecular weight can include, without limitation, nephelometry, specific gravity, chromatography, osmotic pressure, light scattering, and electrophoresis. The extent of degradation in one embodiment is at least 50 percent at two weeks. The extent of degradation in one embodiment is at least 60 percent at two weeks. The extent of degradation in one embodiment is at least 70 percent at two weeks. The extent of degradation in one embodiment is at least 80 percent at two weeks. The extent of degradation in one embodiment is at least 90 percent at two weeks. The extent of degradation in one embodiment is at least 50 percent at three weeks. The extent of degradation in one embodiment is at least 60 percent at three weeks. The extent of degradation in one embodiment is at least 70 percent at three weeks. The extent of degradation in one embodiment is at least 80 percent at three weeks. The extent of degradation in one embodiment is at least 90 percent at three weeks.

A "hydrogel" refers to a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking.

In one embodiment the biodegradable amorphous carrier is not crosslinked. For example, in some methods known in the art, certain hydrogels are combined and then photopolymerized to encapsulate cells and to create a three-dimensional scaffold. See, e.g., Bryant S J et al. (2003) *J Biomed Mater Res* 64A:70-9; Bryant S J et al. (2002) *J Biomed Mater Res* 59:63-72.

In one embodiment the biodegradable amorphous carrier is a hydrogel chosen from type I collagen, type III collagen, type IV collagen, dextran, hyaluronan, or other carbohydrate, chondroitin sulfate, polyethylene glycol (PEG), other biodegradable synthetic polymer, and any combination thereof. In one embodiment the biodegradable amorphous carrier includes type I collagen. In one embodiment the biodegradable amorphous carrier includes dextran beads. The biodegradable amorphous carrier is generally selected such that its initial mean molecular weight is greater than the molecular weight cut-off of the semi-permeable membrane used in a method of the invention. However, as described below, the initial mean molecular weight of the biodegradable amorphous carrier can in at least one circumstance be selected to be less than the molecular weight cut-off of the semi-permeable membrane used in a method of the invention.

As used herein, a cell space for receiving cells refers to the interior of a container into which the population of cells and the biodegradable amorphous carrier are placed and, with respect to the cells, immediately confined for in vitro culture. In one embodiment the cell space for receiving cells is a tube made of a semi-permeable membrane as described herein. In one embodiment the cell space for receiving cells is a pouch made of a semi-permeable membrane as described herein. In each of these embodiments the cell space for receiving the cells includes a closable opening for receiving the cells, for example by pipeting the cells into the tube or pouch. The closable opening can be sealed shut by any suitable method known in the art, including for example, mechanically clamping, tying, heat sealing, and the like.

As used herein, a semi-permeable membrane refers to any suitable porous wall material that permits passage of certain molecules or solutes but not others. The semi-permeable membrane can be homogeneous or nonhomogeneous with respect to the spatial distribution of pores over its surface. The semi-permeable membrane can be homogeneous or nonhomogeneous with respect to the distribution of pore sizes over its surface. In one embodiment the semi-permeable membrane is essentially homogeneous in terms of both the spatial distribution and the pore size over the surface of the membrane. Examples of such semi-permeable membranes are well known in the art and include, without limitation, dialysis membranes, filter membranes, and the like. In one embodiment the membrane is shaped into a tube. In one embodiment the membrane is shaped into a pouch.

The permeability of a solute is dependent upon the shape of the molecule, its degree of hydration and its charge. Each of these may be influenced by the nature of the solvent, the pH and the ionic strength. Generally, molecular size can be conveniently expressed in terms of molecular weight. Semi-permeable membranes with well characterized molecular weight cut-offs are known in the art, are commercially available, and include the dialysis membranes, dialysis tubing, and filter membranes mentioned above. For use in the instant invention, the membrane material will generally be compatible for use in tissue culture and can include, for example, semi-permeable membrane made of regenerated cellulose, cellulose ester, or polyvinylidene difluoride (PVDF; Spectra/Por®, Spectrum Laboratories, Inc., Rancho Dominguez, Calif.). PVDF membranes and tubing are autoclavable and heat sealable. Typical applications for using dialysis membranes include removal of salts, surfactants, detergents and solvents; buffer and pH adjustment of sample solutions; concentration of proteins, peptides or antibodies; DNA electroelution; preparation of proteins prior to electrophoresis, high pressure liquid chromatography (HPLC); removal of contaminating micromolecules; binding studies; and tissue culture extract purification.

The semi-permeable membranes have defined molecular weight cut-offs. Commercially available semi-permeable membranes include those with nominal molecular weight cut-offs ranging from 100 Daltons (0.1 kDa) to 1,000,000 Daltons (1000 kDa). Dialysis membrane pore sizes are generally expressed in terms of the molecular weight at which 90% of solute will be retained by (prevented from permeating) the membrane. In one embodiment the semi-permeable membrane pore sizes are expressed in terms of the molecular weight at which at least 90% of solute is retained by (prevented from permeating) the membrane.

In one embodiment the semi-permeable membrane is charge-neutral, i.e., it carries essentially no net electrical charge itself. Such a membrane allows passage of solute molecules based on their molecular size without regard to their charge. In one embodiment the semi-permeable membrane carries a net positive charge. In one embodiment the semi-permeable membrane carries a net negative charge. In one embodiment the net charge is provided by a coating that is applied to an underlying charge-neutral membrane. The charge or coating can be present on both sides or just one side of the membrane, for instance the inside of a membrane in the shape of a tube. For example, in one embodiment the semi-permeable membrane carries a net positive charge and is a semi-permeable membrane that is coated with poly-L-lysine. The net positive charge acts to repel positively charged solutes, including solutes that might otherwise by size alone pass through the membrane.

As used herein, an in vitro-expanded population of cells in contact with a biodegradable amorphous carrier refers to an in vitro tissue culture product that includes a population of cells that is greater in number than an initial population of said cells placed into culture, wherein the cells are in contact with a biodegradable amorphous carrier as described herein. The biodegradable amorphous carrier includes degradation products of the amorphous carrier retained within the confines of the cell space by the semi-permeable membrane. In one embodiment the in vitro-expanded population of cells in contact with a biodegradable amorphous carrier further includes extracellular matrix material elaborated by the cells and retained within the confines of the cell space by the semi-permeable membrane. Such latter product as used herein is termed a cell/matrix composition produced according to a method of the invention. This tissue culture product is generally amorphous so that it can be introduced as a gel or viscous liquid into a rigid container such as a syringe or trocar and extruded through an opening in the rigid container.

As used herein, cartilage refers to a specialized, avascular form of connective tissue that includes chondrocytes and extracellular fibers embedded in an amorphous, gel-like matrix elaborated by the chondrocytes. Cartilage provides the basis for the formation of long, weight-bearing bones, as well as for articular surfaces. Three major types of cartilage are hyaline cartilage, elastic cartilage, and fibrocartilage, of which hyaline cartilage is most common. In addition to being present on joint surfaces of long bones, hyaline cartilage can be found in the adult on the ventral ends of ribs, in tracheal rings, and in the larynx. Histologically, hyaline cartilage appears as isolated chondrocytes surrounded by and encapsulated in a predominant extracellular hyaline matrix that is rich in mucopolysaccharides (e.g., chondroitin sulfate) and collagen, particularly type II collagen. Perhaps because of its avascular nature, cartilage is generally limited in its ability to heal.

More than nineteen types of collagen have been identified, of which types I, II, III, and IV are best characterized. Type I collagen, the most abundant form, is found in skin, ligaments, tendons, bone, and aorta, and is composed of two identical α1(I) chains and one α1(II) chain. Type II collagen, which forms arcades of thin fibrils and accounts for roughly 40-50 percent of the dry weight of cartilage, is composed of three identical α1(II) chains. Type III collagen, which is found principally in large blood vessels such as aorta, and in lesser amounts in skin, ligaments, and tendons, is composed of three identical α1(III) chains. Nonfibrillar type IV collagen is present in basement membranes.

As used herein, an articular cartilage surface refers to any aspect of a layer of hyaline cartilage overlying an articular surface of a diarthrodial (movable, synovial-lined) joint. An articular surface includes any portion of a joint surface that is involved in the full natural range of motion of a given joint.

As used herein, a damaged articular cartilage surface refers to any articular cartilage surface that is physically defective for any reason. For example, the articular cartilage surface can be acutely damaged, for example by traumatic injury, or the articular cartilage surface can be chronically damaged, for example by repetitive impact loading or stress injury, any inflammatory process, including gout and arthritis (e.g., osteoarthritis), infection, autoimmune disease (e.g., rheumatoid arthritis), aseptic necrosis, and sickle cell anemia. The damage can take the form of a thinning or a disruption of the articular cartilage surface as compared to a normal articular cartilage surface, such as may be present in a corresponding contralateral joint. A normal articular cartilage surface can be defined with reference to any undiseased or uninvolved corresponding articular cartilage surface. In one embodiment damaged articular cartilage can be visualized radiographically, including by plane X-ray, computed tomographic (CT) imaging, and magnetic resonance imaging (MRI). For example, radiographic evidence of tibiofemoral or other joint space narrowing is frequently considered to signal articular cartilage thinning.

The effects of hydrostatic pressure on chondrogenesis have been reported, though data interpretation has been made difficult by complicated and inconsistent methodology, such as the use of cartilage discs vs. chondrocytes (suspended or cultured), confined vs. unconfined models, and application of static pressure vs. intermittent (cyclic) pressure. The effects of mechanical stimuli on cartilage and chondrocytes have been tested with custom-designed apparatus in confined and unconfined models, as reviewed by Mow V C et al. (1999) *Osteoarthritis Cartilage* 7:41-58 and by Mizuno S et al. (1998) *Mat Sci Eng C* 6:301-6. In an unconfined model, compressive loading of cartilage introduced tissue deformations and changes in hydrostatic pressure, fluid exudation, and streaming potential. Maroudas A (1975) *Biorheology* 12:233-48; Comper W D et al. (1993) *Biochem J* 289:543-7. This model may also significantly change cell shape. Guilak F et al. (1995) *J Ortho Res* 13:410-21; Guilak F (2000) *Biorheology* 37:27-44.

Experiments in vitro have frequently used discs of cartilage for evaluation of the effects of biophysical forces on cartilage metabolism. Static compression for 12 h at 0-3 MPa revealed an inverse relationship between sulfate and proline incorporation. Gray M et al. (1988) *J Ortho Res* 6:777-92. The effects of hydrostatic pressure on sulfate and proline incorporation in slices of bovine articular cartilage depend on the magnitude and duration of pressure. Hall A et al. (1991) *J Ortho Res* 9:1-10. Application of physiological levels of pressure (5-10 MPa) for 20 sec or 2 h stimulated subsequent matrix synthesis, whereas continuous application of 20 MPa for 2 h decreased matrix synthesis. Ibid. Biosynthetic responses to dynamic or intermittent compression, however, may be either stimulated or inhibited depending on the frequency and the amplitude of loading. Sah R L Y et al. (1989) *J Orthop Res* 7:619-36; Ostendorf R H et al. (1994) *J Rheumatol* 21:287-92; Palmoski M J et al. (1984) *Arthritis Rheum* 27:675-81; Klein-Nulend J et al. (1987) *J Biol Chem* 262:15490-5; Torzilli P A et al. (1997) *J Biomech* 30:1-9; Buschmann M D et al. (1996) *J Cell Sci* 109:499-508; Mankin K P et al. (1998) *J Pediatr Orthop* 18:145-8.

Pressure-induced strain and subsequent streaming potential may be potent stimulators of ECM synthesis. Kim Y et al. (1994) *Arch Biochem Biophys* 311:1-12; Bachrach N M et al. (1998) *J Biomech* 31:445-51; Kim Y J et al. (1995) *J Biomech* 28:1055-66. However, the solid matrix of articular cartilage is incompressible when subjected to hydrostatic pressure up to 12 MPa. Bachrach N M et al. (1998) *J Biomech* 31:445-51. Moreover, hydrostatic pressure does not affect cell volume. Bushmann et al. suggested that cartilage tissue deformation was a more potent stimulus than change in cell shape. Buschmann M D et al. (1995) *J Cell Sci* 108:1497-1508. The transduction mechanisms by which hydrostatic pressure affects chondrocytes are unclear, but some effects of hydrostatic pressure have been examined in vitro with cartilage discs and with monolayers of isolated chondrocytes.

Effects of cyclic hydrostatic pressure on cultured chondrocytes and on cartilage discs were compared by Parkkinen et al. (1993) *Arch. Biochem. Biophys.* 300:458-65. Sulfate incorporation was inhibited in cell cultures subjected to 0.5, 0.25, or 0.05 Hz cyclic loads for 1.5 h, but was stimulated in cartilage discs subjected to 0.5 Hz cyclic load for 1.5 h. Bovine chondrocyte cultures subjected to longer loading (20 h) showed stimulation of sulfate incorporation at 0.05 and 0.25 Hz, but inhibition at 0.0167 Hz. Ibid. Those investigators concluded that cell/matrix interactions influence the effects of cyclic hydrostatic pressure on cellular function.

In addition, there are data that support the view that stimulation of metabolism is related to changes in fluid flow and/or cell shape (Guilak F et al. (1995) *J Ortho Res* 13:410-21; Kim Y et al. (1994) *Arch Biochem Biophys* 311:1-12; Bachrach N M et al. (1995) *J Biomech* 28:1561-9; Lammi M J et al. (1994) *Biochem J* 304:723-30) and streaming potential (Kim Y J et al. (1995) *J Biomech* 28:1055-66). Hydrostatic pressure (HP) was applied indirectly to isolated chondrocytes suspended in a medium bath by pressurizing the bath solution in a chamber. Hall A et al. (1991) *J Orthop Res* 9:1-10. Even though that model did not contain accumulated cartilage ECM, the interaction between each cell and HP was simply manipulated. Studies with isolated chondrocytes also showed biphasic effects of pressure on proteoglycan synthesis and aggrecan mRNA expression. Lammi M J et al. (1994) *Biochem J* 304: 723-30. Glycosaminoglycan (GAG) accumulation within a three-dimiendional scaffold exposed to 500 or 1000 pounds per square inch (psi) intermittently (5 sec pressurized and 15 sec depressurized for 4 h per day up to 5 weeks) was greater than with no pressure. Hall A et al. (1991) *J Orthop Res* 9:1-10.

Studies with isolated chondrocytes also showed that effects on proteoglycan synthesis and aggrecan mRNA expression depended on the mode of pressure. Lammi M J et al. (1994) *Biochem J* 304:723-30. GAG synthesis does not depend directly on transcription and translation according to Smith et al., who reported that constant pressure loading at 10 MPa for 4 h stimulated collagen type II and GAG synthesis by chondrocytes in high-density monolayer cultures without effects on mRNA levels, whereas intermittent pressure increased the aggrecan mRNA level by 31% and the collagen mRNA level by 36%. Mueller S M et al. (1999) *J Bone Min Res* 14:2118-26.

Articular cartilage consists of chondrocytes and two major macromolecules; i.e., collagen and proteoglycans, which are synthesized by and deposited around the chondrocytes. The chondrocytes also synthesize the synovial fluid which bathes the articular cartilage. In healthy conditions, articular cartilage forms a smooth surface between articulating bone ends to reduce friction caused by movement. This friction is further reduced by the synovial fluid. The structural integrity of the articular cartilage is the foundation of optimal functioning of the skeletal joints in the hips, knees, shoulders, and elbows, among others. Impaired function of skeletal joints dramatically reduces mobility and impairs common activities such as rising from a sitting position or climbing and descending stairs.

To maintain the structural integrity and the proper functioning of the articular cartilage, the chondrocytes constantly synthesize collagen and proteoglycans, the major components of the articular cartilage, as well as the friction-reducing synovial fluid. This constant synthesis of the macromolecules and synovial fluid provides the articular cartilage with the repairing mechanism for most of the usual wear caused by friction between the bone ends.

2. In Vitro Culture Methods

The invention in one aspect provides a method of culturing cells in vitro. The method according to this aspect of the invention includes the steps of contacting a population of cells selected for in vitro culture with a biodegradable amorphous carrier, placing the contacted population of cells in a cell space for receiving the cells, said cell space being bounded at least in part by a semi-permeable membrane having a molecular weight cut-off greater than 100 kDa and up to 1,000 kDa, and periodically applying pressure to the contacted population of cells. The method has several advantages over existing in vitro culture methods, particularly for use with cells which elaborate an ECM. These advantages include, without limitation, the ability to increase ECM production, the ability to produce a tissue that is more nearly like native tissue in terms of its biomechanical properties, selective retention of high molecular weight ECM components, and protection of the cells from direct fluid shear stress.

The method of in vitro culture according to the invention can be used to prepare a cell/matrix construct which can be used as an injectable paste to fill and thereby repair a site of degenerated naturally occurring cell/matrix in subject, e.g., in a site of damaged cartilaginous tissue.

Tissue cells and/or tissue precursor cells can be obtained or derived directly from a donor, e.g., a patient's own cells, from a culture of cells from a donor, from isolated stem cells, or from established cell culture lines. In various embodiments the donor is a mouse, rat, rabbit, guinea pig, hamster, cow, pig, horse, goat, sheep, dog, cat, or human. Cells of the same or different species and preferably of the same immunological profile can be obtained by biopsy, either from the subject or a close relative, e.g., a biological parent or sibling.

If cells are used that may elicit an immune reaction, such as cells from an immunologically distinct donor of the same species as the recipient, then the recipient can be immunosuppressed as needed, for example, using a schedule of corticosteroids and other immunosuppressant drugs such as cyclosporine. However, the use of autologous cells will avoid such an immunologic reaction and the need for such immunosuppressive treatment.

Cells can be obtained directly from a donor, washed, and suspended in a selected hydrogel before being delivered into a cell culture space. The cells can be added or mixed with the hydrogel just prior to their insertion into the cell culture space. Alternatively, the cells and amorphous carrier can be introduced into the cell culture space separately and sequentially, either with cells first and carrier second, or vice versa, provided the cells and carrier can be thoroughly intermingled once they are both within the cell culture space. In addition, cell growth can be enhanced by addition to the in vitro culture medium suitable growth factors or other tissue culture components that specifically or nonspecifically support growth of a selected cell type.

Cells obtained by biopsy can optionally be harvested, cultured, and then passaged as necessary to remove contaminating, unwanted cells, prior to use in the in vitro culture method of the invention.

Chondrocytes can be isolated following aseptic excision from a donor site or source and then digested using a solution of 0.2% collagenase type II (Gibco) and 5% fetal bovine serum (Gibco) in Dulbecco's modified Eagle's medium (DMEM, Gibco) without additives for up to 17 h at 37° C. on an orbital shaker. The solution can then be filtered through a 70 mm nylon cell strainer and centrifuged at 1000 rpm for 10 min. Following aspiration or decantation of the supernatant, the pellet is resuspended in phosphate buffered saline (PBS, Gibco) supplemented with 1% penicillin-streptomycin (Gibco) and 0.02% ethylenediamine-tetraacetic acid (EDTA, Aldrich). The solution is then centrifuged an additional two times and resuspended in PBS. Chondrocyte number and viability are determined using trypan blue exclusion and a hemacytometer.

The number of cells to be placed into culture can vary, depending on the type of cells, the volume of neo-tissue that is desired, and the amount of time in culture. In typical usage, the number of cells to be placed into culture is determined by the volume of the cell culture space, i.e., is determined as an initial or inoculation cell density. For example, the number of cells to be placed into culture can typically range from about $1\times10^6$ to $1\times10^9$ cells/ml, and more typically will range from about $1\times10^7$ to $1\times10^8$ cells/ml. As the cells grow and divide in culture, the overall cell density will increase accordingly.

In one embodiment the cells include chondrocytes and, optionally, precursor cells thereof. For example, under proper conditions, fibroblasts can be made to differentiate into chondrocytes; fibroblasts thus may be considered to be chondrocyte precursor cells. Other cells may be chondrocyte precursor cells, including mesenchymal stem cells.

In one embodiment all or essentially all the cells are chondrocytes. The type of cells present can be assessed by any suitable method, including, for example, by histologic examination, cell surface protein analysis, biochemical or other ECM characterization, fluorescence-activated cell sorting (FACS), nuclear transcript analysis, enzyme-linked immunofluorescence assay (ELISA), Western blotting, immunohistochemistry, electron microscopy, reverse transcriptase-polymerase chain reaction (RT-PCR) analysis, and other methods known to those of skill in the art.

The biodegradable amorphous carrier is any suitable natural or synthetic material that is biocompatible and that is substantially to fully biodegradable over the course of weeks to months. In one embodiment the amorphous carrier includes type I collagen, for example as a 0.3 percent solution (w/v) of type I collagen in culture medium or other physiologically acceptable fluid. Type I collagen is commercially available in various forms. The type I collagen can be isolated from unwanted salts, preservatives, or other agents prior to use in the method of the invention, using standard techniques involving solvent exchange. Such techniques may include, for example, centrifugation, ultrafiltration, dialysis, and the like.

In certain embodiments the biodegradable amorphous carrier is or includes dextran beads. In various embodiments the biodegradable amorphous carrier includes a hydrogel chosen from dextran, chondroitin sulfate, polyethylene glycol, hyaluronan, and any combination thereof. Each of these may be selected on the basis of their molecular weight, so as to be suitable for use with a particular molecular weight cut-off semi-permeable membrane as described herein. More specifically, the starting molecular weight of the biodegradable amorphous carrier is selected such that it will be substantially retained within the cell culture space by the semi-permeable membrane. While larger molecular weight forms of the biodegradable amorphous carrier will not permeate the membrane, smaller molecular weight degradation products of the biodegradable amorphous carrier will, as they are formed, permeate the membrane and thereby exit the cell culture space and be lost into the culture medium.

In certain embodiments the cell culture space for receiving the cells is a semi-permeable membrane tube or pouch, for example a dialysis tube, having a closable opening for receiving the cells and the carrier. After the cells and carrier are introduced into the cell culture space, and the closable opening is closed by any suitable method so that the entire resulting structure (i.e., the closed semi-permeable tube or pouch containing cells and carrier) can be immersed in or otherwise placed in contact with a suitable culture medium.

The molecular weight cut-off (MWCO) size of the semi-permeable membrane is selected to retain cells, ECM, and high molecular weight components of the biodegradable amorphous carrier, while permitting exchange of low molecular weight degradation products of the carrier, nutrients, waste products, and gases with the culture medium. Of course the low molecular weight degradation products of the carrier, nutrients, waste products, and gases will generally flow down their concentration gradients such that, for example, low molecular weight degradation products of the carrier exit from the cell culture space. Ideally the MWCO size of the membrane is selected based on knowledge of the initial molecular weight and biodegradation kinetics of the carrier. For example, carriers with relatively rapid degradation may best be used with a semi-permeable membrane with a smaller MWCO than would be used for carriers with relatively slow degradation, so that the kinetics of elimination of high molecular weight carrier and elaboration of high molecular weight ECM are similar. The selection of MWCO can be made without undue experimentation, using techniques described in the examples below.

Thus in one embodiment the semi-permeable membrane has a MWCO of at least 200 kDa. In one embodiment the semi-permeable membrane has a MWCO of at least 250 kDa. In one embodiment the semi-permeable membrane has a MWCO of at least 300 kDa. In one embodiment the semi-permeable membrane has a MWCO of at least 400 kDa. In one embodiment the semi-permeable membrane has a MWCO of at least 500 kDa. In one embodiment the semi-permeable membrane has a MWCO of at least 600 kDa. In one embodiment the semi-permeable membrane has a MWCO of at least 700 kDa. In one embodiment the semi-permeable membrane has a MWCO of at least 800 kDa. In one embodiment the semi-permeable membrane has a MWCO of at least 900 kDa. In one embodiment the semi-permeable membrane has a MWCO of 1,000 kDa.

In some embodiments the semi-permeable membrane can be treated so as to carry a net positive or negative charge, thereby affecting the flux of appropriately sized similarly charged and oppositely charged solutes across the membrane. In one embodiment the semi-permeable membrane carries a net positive charge. In one embodiment the semi-permeable membrane is coated with a cation or polycation, such as poly-L-lycine. In the case of dialysis tubing, such coating can be conveniently accomplished by simply soaking the membrane in a solution of the poly-L-lycine.

At resting conditions, large molecules such as albumin are essentially excluded from proteoglycan aggregates. Ogston A G et al. (1973) *Proc R Soc Lond A* 333:297-316. It was reported that cyclic loading of 2.8 MPa in articular cartilage discs significantly enhanced transport of albumin. O'Hara B P et al. (1989) *Ann Rheum Dis* 49:536-9. Once chondrocytes accumulate pericellular ECM, the ECM may physically prevent soluble factors from binding to cell surface receptors. Ogston A G et al. (1973) *Proc R Soc Lond A* 333:297-316. Therefore, it is expected that accumulation of pericellular matrix will impair the availability of mitogens in culture over time, and that hydrostatic pressure may assist the transport of required regulatory factors.

Compared with other large molecules, proteoglycan, a major cartilage ECM component, has a high osmotic pressure. Proteoglycan aggregates (aggrecan) have a large number of fixed anions of $-COO^-$ and $-SO_3^{3-}$ that interact with free cations such as $Na^+$ and $Ca^{2+}$. As more proteoglycan accumulates, osmotic pressure increases. Moreover, the increase in osmotic pressure results in swelling tension of the proteoglycans surrounding a cell. Osmotic pressure is generated with a gradient of osmolite between the inside and outside of the pouch (perfused media phase). The balance of these pressures would be expected to affect tissue morphogenesis and histogenesis.

Through the semi-permeable membrane, osmotic pressure in the medium will be altered with the addition of abundant ECM components such as chondroitin sulfate and dextran sulfate (of a defined molecular weight). Externally applied hydrostatic fluid pressure and internally generated osmotic pressure alter mass transfer of solutes. The influence of the ECM surrounding the chondrocytes needs to be considered in the balance between hydrostatic and osmotic pressures. The in situ osmotic pressure of the surface and calcified zones of the human femoral head are 310 to 370 mOsm and 370 to 480 mOsm, respectively. ECM osmotic pressure of native cartilage is higher than that of regular culture medium. Osmotic pressure in the culture medium can be varied with the addition of chondroitin sulfate or dextran.

The method of in vitro culture includes the application of pressure to the population of cells in culture. The pressure is typically applied as hydrostatic fluid pressure, which is transmissible through the membrane, at levels of about 0.5 to about 5 MPa. Physiologic levels of pressure, which can range between 5-10 MPa, are also contemplated by the invention. Whereas proliferation of chondrocytes in carrier under conditions of static culture conditions (i.e., ambient atmospheric pressure) was minimal, application of hydrostatic pressure to chondrocytes in carrier results in improved cell proliferation and ECM production by the cells. In one embodiment the pressure is applied as 0.5 to 3.5 MPa hydrostatic fluid pressure at 0.001 to 1 Hz.

3. Culture Device

An apparatus useful for practicing the in vitro culture methods of the invention is disclosed in U.S. Pat. No. 6,432,713, the entire contents of which are incorporated herein by reference. Briefly, as disclosed in U.S. Pat. No. 6,432,713, an apparatus for cultivating a cell or tissue according to the invention is characterized by including a culture unit (culture circuit unit) having a culture chamber containing therein a cell or tissue and supplying culture medium, pressure application means (pressure application apparatus) for applying a pressure to the cell or tissue in the culture chamber, and culture medium supply means (culture medium supply apparatus) for intermittently or continuously supplying the culture medium to the culture unit.

That is, the culture unit accommodates the cell or tissue to be cultivated in the culture chamber to supply a culture medium needed for the cell or tissue that is isolated from the open air. The cell or tissue that is isolated from the open air is protected from contamination by bacteria and so forth, and hence it grows to a tissue having an excellent quality. A desired pressure by pressure application means in addition to physical stimulation caused by a hydraulic pressure and a flow by the culture medium is applied to the cell or tissue. As a result, it affects metabolism function, cell division cycle, concentration gradient or dispersion of living body stimulation so that the culture is enhanced. The mode of supply of the culture medium to the cell or tissue is arbitrarily set by the culture medium supply means, and the culture medium can be supplied to the cell or tissue intermittently or continuously so that the culture is enhanced by a variety of physical stimulation. The mode of the supply of the culture medium includes one of or both of the supply of a new culture medium at all times or the supply of the culture medium by repetitively circulating the culture medium. In the mode of circulation of the culture medium can save the culture medium, but there is an advantage of the prevention of the variation in concentration of the culture medium when supplying the culture medium in one direction.

In one embodiment the apparatus for cultivating a cell or tissue according to the invention is characterized in further providing control means for controlling the pressure application means or culture medium supply means. That is, although the pressure application means or culture medium supply means can be controlled arbitrarily, various controls such as a feedback control or feed forward control and a program control and so forth can be performed by use of control means such as a computer. It is needless to say to add a personal collection control by an interruption, and the collection control is not excluded.

In one embodiment the apparatus for cultivating a cell or tissue according to the invention is characterized in that the pressure applied from the pressure application means to the cell or tissue can be arbitrarily set depending on the cell or tissue. The manner of applying a pressure, namely, a pressure pattern, is set, corresponding to a cell or tissue to be cultivated, thereby performing an efficient culture.

In one embodiment the apparatus for cultivating a cell or tissue according to the invention is characterized in that the pressure applied from the pressure application means to the cell or tissue is a pressure which is varied intermittently, a pressure which is repeated every given time, or a pressure which increases or decreases every given time. That is, the pressure pattern can be conceived in all modes, thereby cultivating cell or tissue efficiently by selecting a mode of pressure pattern.

In one embodiment the apparatus for cultivating a cell or tissue according to the invention is characterized in that the culture unit is independent of and detached from a culture apparatus body. That is, the culture unit having the culture chamber for accommodating therein the cultivated cell or tissue can be independent of and detached from a culture apparatus body so that the cell or tissue can be moved together with the culture unit that is separated from the open air to protect the cell or tissue from being contaminated by bacteria during the motion thereof.

In one embodiment the apparatus for cultivating a cell or tissue according to the invention is characterized in that the culture unit is accommodated in a hermetically sealed space that is isolated from open air. That is, since the hermetically sealed space is the culture space, and it is isolated from open air, it is possible to set a culture environment by the supply of the desired gas, to protect the cell or tissue from the contamination by the open air.

In one embodiment the apparatus for cultivating a cell or tissue according to the invention is characterized in that the culture apparatus further includes gas absorption means capable of absorbing a nitrogen gas, an oxygen gas, a carbon dioxide gas. That is, any one or combination of a nitrogen gas, an oxygen gas, or a carbon dioxide gas can be supplied to the culture unit accommodated in the hermetically sealed space and the gas absorption means is provided in the culture unit so that the gas is applied to the cell or tissue and a living environment can be mimicked by supplying and controlling gas.

In one embodiment the apparatus for cultivating a cell or tissue according to the invention is characterized in that the hermetically sealed space is filled with a nitrogen gas, an oxygen gas, a carbon dioxide gas. That is, when a nitrogen gas, an oxygen gas, a carbon dioxide gas is filled in the culture space formed by the hermetically sealed space, a living body environment can be mimicked.

In one embodiment the apparatus for cultivating a cell or tissue according to the invention is characterized in further including a culture medium tank for storing therein the culture medium to be supplied to the culture unit. That is, the culture medium supply source is needed for supplying or circulating a necessary culture medium to the culture unit, and the culture medium tank is a supply source. Particularly, it is possible to prevent the culture medium held in the culture unit from being contaminated, if the culture medium tank is installed in the hermetically sealed space that is isolated from the open air.

In one embodiment the apparatus for cultivating a cell or tissue according to the invention is characterized in that the culture chamber includes a pressure-transmitting film for receiving a pressure from the outside. That is, it is possible to apply pressure application stimulation to the cell or tissue accommodated in the culture chamber in a state wherein it is isolated from open air, and to realize desired pressure application stimulation such as stimulation mimicking a living body environment by providing the pressure-transmitting film.

In one embodiment the apparatus for cultivating a cell or tissue according to the invention is characterized in that the culture chamber includes pressure buffering means. That is, it is possible to realize physical stimulation similar to a living body environment and to enhance the culture of the cell or tissue by regulating a pressure by pressure buffering means when a part of a culture unit is pressurized.

In one embodiment the apparatus for cultivating a cell or tissue according to the invention is characterized in that the apparatus further includes a pressure chamber fixed to the culture chamber by way of a pressure-transmitting film, and a pressure is applied to the cell or tissue in the culture chamber by allowing a hydraulic pressure, an oil pressure or an air pressure to act on the cell or tissue in the culture chamber. That is, it is possible to realize desired pressure application stimulation and to mimic a living body environment with high accuracy by using any of the hydraulic pressure, the oil pressure, or the air pressure as pressure forming means.

In one embodiment the apparatus for cultivating a cell or tissue according to the invention is characterized in that the culture medium supply means includes a medium supply chamber provided in the culture unit and a medium supply unit for pressuring a culture medium that is taken in the medium supply chamber and supplying the pressurized culture medium. That is, the culture medium supply means is means for supplying and circulating the culture medium in the culture unit, and it is formed of various types, for example, if it is formed of the medium chamber and the medium supply unit for pressuring a culture medium that is taken in the medium supply chamber, the amount of applied pressure can be controlled to set a desired amount of supply medium.

In one embodiment the apparatus for cultivating a cell or tissue according to the invention is characterized in that a relief valve is provided in the culture, and when a pressure of the culture medium exceeds a given pressure which is arbitrarily set to the relief valve, the relief valve is opened to decrease the pressure of the culture medium. That is, it is important to buffer the pressure to be applied to the culture for applying ideal pressure application stimulation to the cell or tissue. If the pressure relieve valve is used as one means, and it is opened to decrease the pressure of the culture medium when the pressure of the culture medium exceeds a given pressure which is arbitrarily set to the relief valve, the culture medium is controlled in an ideal pressure state without contaminating the culture medium.

In one embodiment the apparatus for cultivating a cell or tissue according to the invention is characterized in that heating means or humidifying means are provided in a hermetically sealed space and the hermetically sealed space is kept and controlled at a desired temperature or humidity. That is, it is possible to provide a culture space conforming to a living body environment by controlling a temperature and a humidity of the hermetically sealed space in which the culture unit is accommodated.

In one embodiment the apparatus for cultivating a cell or tissue according to the invention is characterized in that a sound producing unit for applying an ultrasonic wave or the like sound wave in the culture chamber in the culture unit. That is, it is possible to mimic a living body environment acoustically by using the sound producing unit together because a living body receives acoustic stimulation from the outside, and possible to inject the cell or tissue to be cultivated in a culture chamber by use of an ultrasonic wave together with high reliability.

In one embodiment the apparatus for cultivating a cell or tissue according to the invention is characterized in that the apparatus further includes a control means for controlling concentration of a gas to be supplied to the hermetically sealed space. That is, it is possible to mimic a living body environment to enhance the culture of the cell or tissue by controlling the concentration of a gas to be supplied to the hermetically sealed space by the control means.

4. Compositions

The invention in certain aspects provides compositions that are produced according to the in vitro culture methods of the invention. These compositions generally include in vitro-expanded populations of cells that are in contact with a biodegradable amorphous carrier and contained within a cell space bounded at least in part by a semi-permeable membrane. The compositions of the invention can be used in the clinical methods of the invention, e.g., to treat damaged tissue in a subject.

In one aspect the invention provides a composition that includes an in vitro-expanded population of cells in contact with a biodegradable amorphous carrier. The population of cells in one embodiment includes chondrocytes and, optionally, precursor cells thereof. In one embodiment the cells consist essentially of chondrocytes. The biodegradable amorphous carrier can be as previously described herein, including, without limitation, type I collagen, dextran beads, dextran, chondroitin sulfate, PEG, hyaluronan, or any combination thereof. In addition to the foregoing, the biodegradable amorphous carrier according to these aspects of the invention encompasses the remaining high molecular weight material derived from biodegradable amorphous carrier material placed in contact with the population of cells at any point in the in vitro culture. In a typical embodiment the remaining biodegradable amorphous carrier according to this aspect of the invention encompasses the remaining high molecular weight material derived from biodegradable amorphous carrier material placed in contact with the population of cells at the beginning of the in vitro culture. For example, the population of cells can be maintained in culture over a period of days to weeks, typically one week to six weeks, more typically three to six weeks, and most typically three to four weeks, during which time the biodegradable amorphous carrier can be degraded to a significant extent, up to about but not including 100 percent. In one embodiment the biodegradable amorphous carrier is type I collagen.

In one aspect the invention provides a cell/matrix composition produced according to an in vitro culture method of the invention. In one embodiment according to this aspect of invention, a population of chondrocytes, with or without chondrocyte precursor cells, is cultured as described to yield an in vitro-expanded population of chondrocytes plus high molecular weight extracellular matrix material elaborated by the chondrocytes, along with retained biodegradable amorphous carrier, wherein optionally the cells, matrix material, and carrier are contained within a cell space for receiving the cells, wherein the cell space is bounded in whole or in part by a semi-permeable membrane having a molecular weight cut-off in excess of 100 kDa. In various embodiments the semi-permeable membrane has a molecular weight cut-off chosen from greater than 100 kDa to 1,000 kDa; 200 kDa to 1,000 kDa; 250 kDa to 1,000 kDa; 500 kDa to 1,000 kDa; and 1,000 kDa. The biodegradable amorphous carrier according to this aspect of the invention is as described above and can include, without limitation, any one or combination of type I collagen, dextran beads, dextran, chondroitin sulfate, PEG, hyaluronan, and high molecular weight degradation products thereof. In one embodiment the biodegradable amorphous carrier is type I collagen. The population of cells can be maintained in culture over a period of days to weeks, typically one week to six weeks, more typically three to six weeks, and most typically three to four weeks.

When the cell/matrix product includes the cell space bounded by semi-permeable membrane, the semi-permeable membrane provides a convenient form of packaging for transport of the cells and their elaborated cell matrix produced according to the in vitro culture method of the invention. For example, when the cell space is in the form of a tube made of semi-permeable membrane, e.g., dialysis tubing, the tube containing the cell/matrix material can be transferred as a unit to a site for clinical use. In addition, such cell/matrix material contained within the tubular semi-permeable membrane can be readily removed from the tube by, for example, opening or cutting off an end of the tube and extruding the enclosed cell/matrix material out of the tube through the open end, like toothpaste from a tube of toothpaste.

5. Clinical Methods

The invention also provides methods for treating damaged cartilaginous tissue in a subject. The methods include a method for treating a damaged articular cartilage surface in a patient. The methods in general terms involve introducing an effective amount of a cell/matrix composition of the invention into a site of damaged cartilaginous tissue or damaged articular cartilage surface, wherein the introduced cell/matrix material is vital and takes up residence as a living graft to replace the damaged tissue, thereby treating the damaged tissue. Because the cell/matrix composition of the invention has, unlike compositions in which there is a scaffold structure, no intrinsic three-dimensional shape of its own, it can be introduced into a tissue space as an extrudable product that readily conforms to the shape defined by the tissue defect it is to fill.

In one aspect the invention provides a method of treating a damaged cartilaginous tissue. The method according to this aspect of the invention involves introducing an effective amount of a chondrocytic cell/matrix composition of the invention into a site of damaged cartilaginous tissue to treat the damaged cartilaginous tissue. The cell/matrix composition can be introduced into the site using any method suitable for the intended purpose. In one embodiment the cell/matrix composition is extruded into the site of damaged cartilaginous tissue, for example using a syringe, cannula, or trocar. In one embodiment the cell/matrix composition can be introduced into the site as part of an open procedure. In one embodiment the cell/matrix composition can be introduced into the site as part of a so-called minimally invasive procedure, e.g., an arthroscopic procedure.

In one embodiment the method is a method for treating a damaged intervertebral disc. Intervertebral discs act as semi-elastic cushions between adjacent vertebral bodies which form the vertebral column. Taken together, the intervertebral discs account for one-fourth of the length of the vertebral column in humans. Each disc consists of a central portion, the nucleus pulposus, and a peripheral part, the anulus fibrosus. The semi-fluid nucleus pulposus in young adults contains a large amount of water and a few cartilage cells; with age, the water content decreases and is replaced by fibrocartilage. The annulus fibrosus is composed of fibrocartilage which normally retains the inner nucleus pulposus and prevents the latter from herniating. Damaged intervertebral discs are common and are associated with acute and chronic back pain, sciatica, muscle weakness, foot drop, paralysis, paraplegia, bladder retention, and other symptoms familiar to those of skill in the medical arts.

The invention in one aspect provides a method of treating a damaged articular cartilage surface. The method according to this aspect of the invention involves the step of introducing an effective amount of a chondrocytic cell/matrix composition of the invention into a space defined by a surface zone cartilage overlying a site of damaged articular cartilage surface and cartilage or subchondral bone beneath the site of damaged articular cartilage surface, to treat the damaged articular cartilage surface. It has been discovered according to the invention that when a defect in an articular cartilage surface is filled with a biodegradable polymer, e.g., a fibrin glue, a thin layer of neocartilaginous cells grows and spreads out over the surface of the glue. Simultaneous to the formation of this surface zone cartilage, the fibrin glue is degraded, such that over time the glue is resorbed, leaving behind just the thin surface zone cartilage overlying the original site of the surface defect. The space previously occupied by the glue can serve as a site for introduction of new cartilage according to the method of the invention. Chondrocytes expanded in vitro according to the in vitro culture methods of the invention can be introduced beneath the surface zone cartilage. The surface zone cartilage helps keep the in vitro-expanded chondrocyte/matrix composition in place while the cells become integrated into the surrounding cartilaginous environment.

In one embodiment the chondrocytes are derived from tissue of the subject to be treated. For example, cells can be harvested from the site of the damaged articular surface at the time of preparing the site, including debridement of the site and introduction of the fibrin glue into the site of the defect. The subject's own cells are then expanded in vitro as described above, while the fibrin glue is undergoing degradation in situ, and then returned to the subject when the cell/matrix composition is suitably expanded or mature. The extent of degradation of the fibrin glue at the time of introduction of the cell/matrix composition can but need not be complete, as the degradation is expected to continue after the introduction of the vital cell/matrix composition.

In one embodiment the chondrocytes are derived from tissue of a donor other than the subject to be treated. The donor can be allogeneic or xenogeneic. For example, cells can be harvested from an articular cartilage surface of a cadaveric or living donor. The donor's cells are then expanded in vitro as described above and then administered to the subject when the cell/matrix composition is suitably expanded or mature.

In one embodiment the step of introducing the cell/matrix composition into the space is performed as part of an arthroscopic or minimally invasive procedure to treat the damaged articular cartilage surface. In one embodiment the step of introducing the cell/matrix composition is performed as a closed procedure under ultrasound or other suitable imaging guidance. In one embodiment a closed procedure can include percutaneous injection into a desired site.

The methods just described can be used to treat any of a number of joints in a subject, including without limitation a joint chosen from knee, hip, shoulder, elbow, wrist/hand (intercarpal, carpometacarpal, intermetacarpal, metacarpophalangeal, interphalangeal), ankle/foot (intertarsal, tarsometatarsal, intermetatarsal, metatarsophalangeal, interphalangeal), and temporomandibular. In one embodiment the damaged articular surface is a damaged articular surface of a knee. In one embodiment the damaged articular surface is a damaged articular surface of a hip.

In one aspect the invention provides a method of treating osteoarthritis in a subject. The method according to this aspect of the invention involves the step of, in a subject having osteoarthritis of a joint, introducing an effective amount of a chondrocytic cell/matrix composition of the invention into a space defined by a surface zone cartilage overlying a site of damaged articular cartilage surface and subchondral bone beneath the site of damaged articular cartilage surface of the joint, to treat the osteoarthritis. In one embodiment the damaged articular surface is a damaged articular surface of a knee. In one embodiment the damaged articular surface is a damaged articular surface of a hip.

The present invention is further illustrated by the following Examples, which in no way should be construed to be further limiting.

EXAMPLES

Example 1

Apparatus for Cultivating Cells or Tissue

Figure 2:
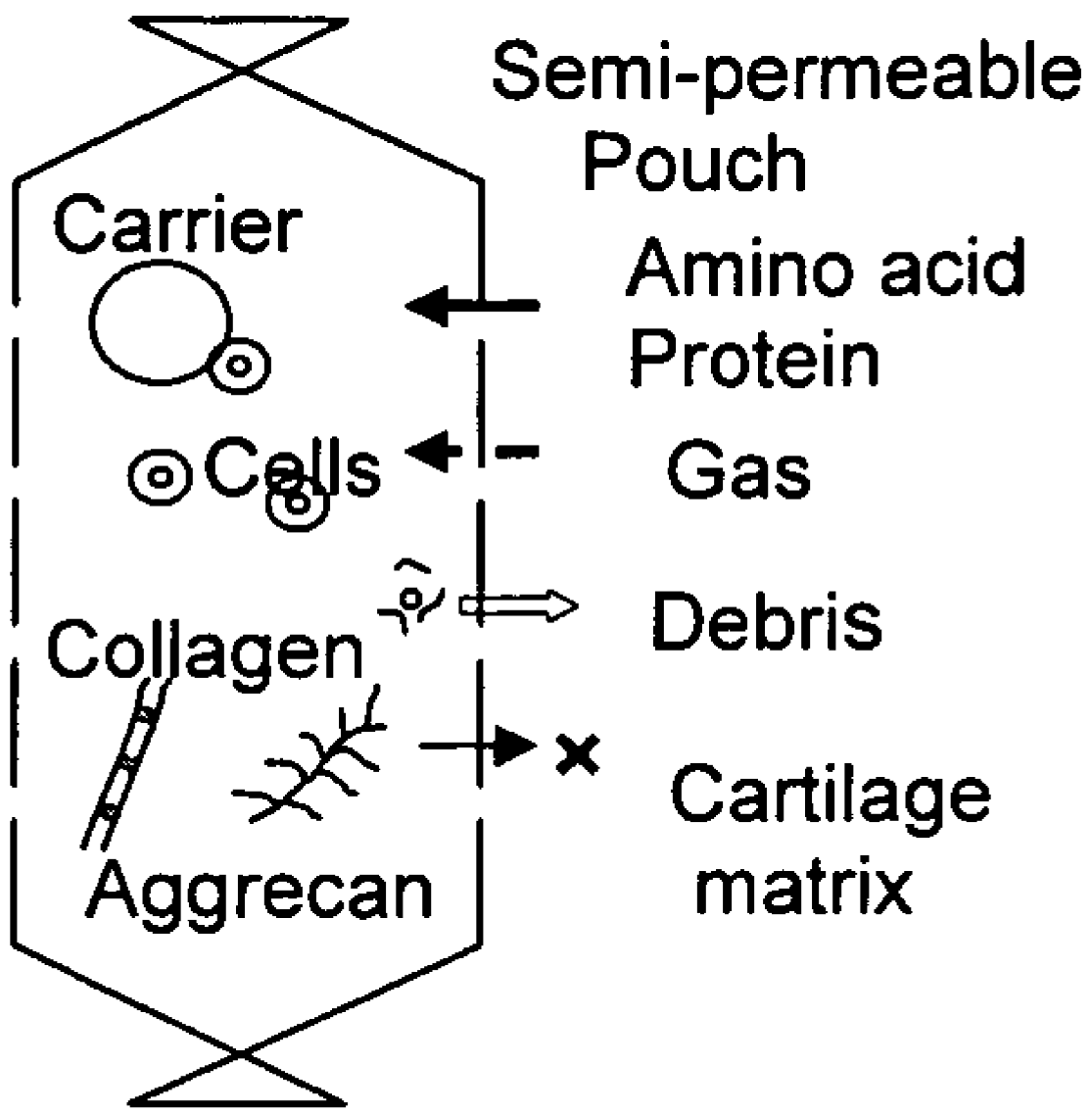
FIG. 2 is a schematic drawing depicting the use of a semi-permeable membrane pouch for the culture of cells in a biodegradable amorphous carrier. Semi-permeable membrane (e.g., dialysis tubing) selectively allows influx and efflux of small molecules (e.g., gas, amino acids, ions, proteins, and degraded debris) and prevents efflux of large molecules (e.g., aggrecan, collagen). With dynamic hydrostatic fluid pressure and constant medium change (perfusion), diffusive mass transfer is promoted and direct fluid shear stress is avoided.

A hydrostatic pressure/perfusion culture system (bioreactor) suitable for use in the in vitro culture methods of the invention is depicted in FIG. 1 and described in U.S. Pat. No. 6,432,713, the entire contents of which are incorporated herein by reference. A schematic drawing depicting the use of a semi-permeable membrane pouch for the culture of cells in a biodegradable amorphous carrier is depicted in FIG. 2. The semi-permeable membrane pouch, containing cells and biodegradable amorphous carrier, is placed within the culture chamber, which is kept horizontal and maintained at 37° C. for a culture period of one to six weeks or more.

Example 2

Evaluation of Mass Transfer of Molecular Markers with Biodegradable Polymers in a Semi-Permeable Membrane Pouch After Application of Hydrostatic Pressure In Vitro Experiments are performed to evaluate the mass transfer of molecular markers in an amorphous cell carrier through a semi-permeable membrane at static culture conditions as well as at different magnitudes and cycles of fluid pressure. Cartilage ECM has high molecular weight and will stay within the semi-permeable membrane pouch. Degraded cell carrier debris (small molecules) and metabolic waste will be exuded into the medium phase. Under static conditions, nutrients can infiltrate the pouch according to Fick's law. In addition, the bioreactor is used to manipulate mass transfer with defined hydrostatic fluid pressure, medium flow, and controlled oxygen/carbon dioxide concentration. As a model of mass transfer, molecular weight markers are used to evaluate mass transfer under a series of experimental conditions (Table 1): 0.3% neutralized collagen type I (Vitrogen, Cohesion), PEG (Coseal, Baxter), and supplemented hyaluronan (Smith & Nephew) are evaluated as possible cell carriers within a defined molecular weight cut-off (MWCO) size semi-permeable membrane pouch. Molecular weight markers of at least 70 kDa, 250 kDa, and 500 kDa of fluorescent FITC- or Rhodamine-dextran (Sigma) are added to the carriers. Since sulfate-GAG (S-GAG) is highly negatively charged, a FITC-dextran (acidic pI) marker is used to mimic a charged molecule. The markers/carrier are injected into a semi-permeable pouch (1 mm inside diameter, 1.2 mm outside diameter, 10 mm length). The pouch is heat-sealed and incubated under static conditions (i.e., at ambient pressure) or with applied hydrostatic pressure. The pouches are harvested at 1, 3, 12, 24, 48, and 74 hours. Samples (markers/carrier material) are then isolated from the pouches. Fluorescence intensity and volume of the samples are measured. Alternatively, the membrane is coated with poly-L-lysine to increase positive charge of the membrane. This may change efficiency of trapping negatively charged cartilage ECM.

TABLE 1

Experimental Conditions and Evaluation Methods

| Culture Conditions | | | |
|---|---|---|---|
| Test carrier materials | Membrane MWCO size | Physical stimuli Hydrostatic pressure | Evaluation |
| Collagen 0.3% | 250 kDa | Static (control) | a) Fluorescent markers 70 kDa, 250 kDa, 500 kDa |
| PEG | 500 kDa | Constant 0.7 MPa | b) Cell viability: Fluorescent Cell toxicity assay |
| Hyaluronan | 1000 kDa | | c) Proliferation: DNA content fluorescent assay (Hoechst) |
| | | Cyclic 0.7 MPa, 0.5 Hz | d) Biosynthetic Phenotype: S-GAG accumulation assay Collagen type II Western blot |
| | | Altered algorithms | e) Catabolic: MMP immunohistology |

Kinetics of molecular weight markers for each culture condition are computed for mass transfer coefficient for each molecular weight. Charge modification of the membrane affects mass transfer with specific charge modification.

Example 3

Figure 3:
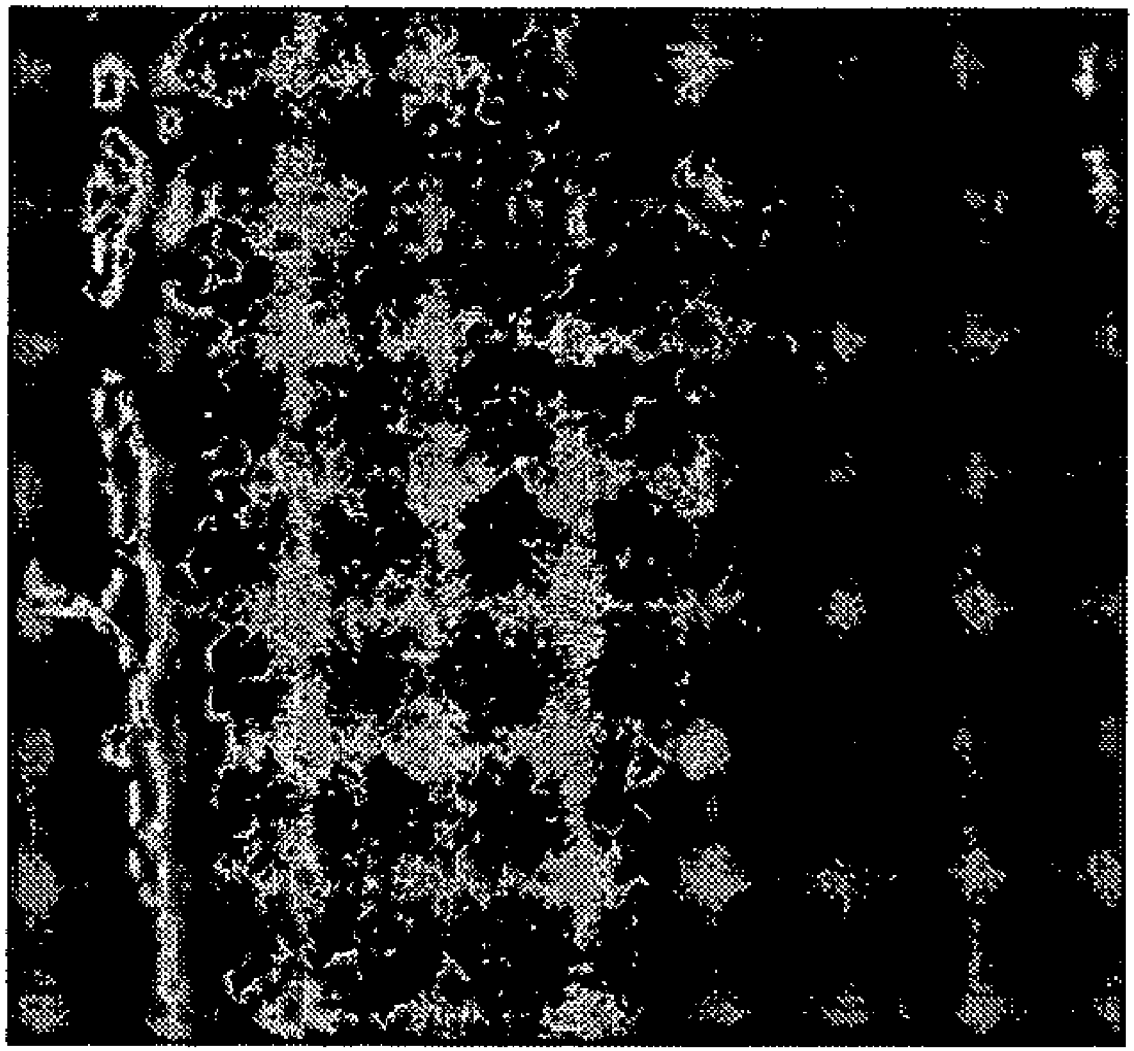
FIG. 3 is a photographic image depicting limited diffusion of the molecular marker (dextran-FITC, 500 kDa) from the surface layer into native bovine articular cartilage.

Effects of Hydrostatic Fluid Pressure on Mass Transfer and Degradation of Amorphous Cell Carrier in Semi-Permeable Membrane Pouch Biodegradable amorphous polymer (hydrogel or sol/gel reversible polymer) is tested at defined cell culture conditions using a tissue culture system. A semi-permeable membrane pouch is used to hold the cell construct and extracellular matrix products of large molecular weight produced by the chondrocytes. Performance of the pouch is analyzed according to molecular weight cut-off size from 100 to 500 kDa under hydrostatic fluid pressure (HFP) ranging 0 to 5 MPa and 0 to 0.5 Hz. The test carrier is injected into the pouch and evaluated in terms of kinetics of degradation. Fluorescent molecular tracers (e.g., dextran-FITC) ranging from 100 to 500 kDa are used as markers. The fluorescence intensity is measured with a fluorometer using suitably selected wavelengths for fluorescence excitation and detection. From a preliminary study it was observed that dextran-FITC at 500 kDa did not penetrate into a native cartilage (FIG. 3). Thus, a <500 kDa molecular marker is suitable for use in this experiment.

Preliminary data indicated that a cross-linked dextran bead-shaped polymer dissolved after 10 days culture in an ordinary culture dish. The beads did not show cytotoxicity although human articular chondrocytes did not adhere to the surface of the beads.

Example 4

Effects of Hydrostatic Fluid Pressure on Cell Proliferation and ECM Production in Semi-Permeable Pouch by Nucleus Pulposus Cells and Chondrocytes Cellular experiments are performed using rabbit nucleus pulposus (NP)-derived cells and discarded human intervertebral disc (hIVD) tissue. Two- to four-week-old freshly killed rabbits are purchased from a local abattoir (USDA authorized). NP and anulus fibrosus (AF) are harvested from the lumbar IVDs. NP- and AF-derived cells are enzymatically isolated separately. Isolated NP and AF cells are seeded into regular culture dishes to expand the cell number. Passage number is minimized for maintenance of phenotype for all tissue.

After 2 to 3 passages, the cells are seeded into a pouch made of semi-permeable membrane (MWCO size: 100 kDa, 250 kDa, or 500 kDa) and incubated under defined conditions of magnitude of hydrostatic fluid pressure (HFP), perfusion rate, and gas concentration using a state-of-the art tissue engineering processor described in U.S. Pat. No. 6,432,713 (FIG. 1). These varied conditions are tested in order to maximize chondrocytic phenotype. From preliminary data, the magnitude of HFP, the cycle frequency, and the medium flow rate are varied in the physiologically relevant ranges of 0-3 MPa, 0-0.5 Hz, and 0.01-1.0 ml/min. Medium flow rate is varied depending on the optimal level of mass transfer of both nutrients and gas. The duration of culture is set from 2 days to 21 days in reference to preliminary data. Biochemical evaluation is used to determine an optimal time point and seeding density.

Discarded human tissue is tested using the same culture system at the optimum culture conditions defined using isolated rabbit NP-derived cells and AF-derived cells. As a validated control, the cells are seeded into collagen gel/sponge construct or with a small amount of collagen gel into the pouch. These methods are standard procedure to promote chondrogenesis with treatment of HFP. In order to maintain quality assurance for any further evaluations, the cell construct is incubated in a culture dish for 1 week.

The source of cells for IVD reconstruction is important because intact autologous NP is difficult to harvest from a patient. Articular cartilage of a patient is one option as a cell source for IVD reconstruction.

From preliminary data, discarded herniated tissue was shown to be fibrotic and needed enzymatic digestion for cell isolation. Human IVD cells are seeded into culture dishes and incubated for approximately for 1-2 week. Adhered IVD cells are seeded into the semi-permeable pouch and incubated at the optimal conditions defined using rabbit IVD-derived cells. From preliminary data, it was shown that exogenous collagen matrix (gel) was degraded. The isolated cells may contain fibroblasts or dedifferentiated chondrocytes. Matrix metalloproteinase (MMP) activities are evaluated histologically and biochemically. A supplement such as ascorbic acid is optionally added to protect against extracellular matrix (ECM) degradation. Other possible supplements to protect against ECM degradation are also tested.

Cartilage matrix production and cellularity is evaluated histologically and biochemically by ELISA. The ECM accumulation from the culture is measured by 1,9-dimethylmethylene blue (DMB) assay for total S-GAG. Collagen type II, aggrecan, and link protein are measured by Western blotting. The extensive molecular evaluation includes aggrecan and type II collagen mRNA expression to define the phenotype of chondrocytic cells. Cell number (DNA concentration) and cellularity are evaluated with Hoechst fluorescent dye and proliferative cell nuclear antigen (PCNA) assay as well as fluorescent cytotoxity assay. Cells are harvested from hydrostatic fluid pressure/perfusion culture and the smeared cells are fixed and stained with monoclonal antibody against PCNA.

Histology. Specimens were fixed with 2% paraformaldehyde in 0.1 M cacodylate buffer (pH 7.4) at 4° C. for 24 h and were embedded in either glycolmethacrylate (JB-4, Polysciences, Warrington, Pa.) or paraffin. Sections of JB-4-embedded samples (20 µm) were stained with 0.2% toluidine blue O (Fisher, Franklin, N.J.) at pH 4.

ELISA. For biochemical measurement of matrix components, frozen sponges were minced into 1-mm$^3$ pieces with a surgical blade. Each of eight replicate samples was extracted for 48 h at 4° C. in 1 ml of 4 M guanidine-hydrochloride, 10 mM EDTA (pH 5.8), with protease inhibitors (0.1 M ε-aminohexanoic acid and 0.005 M benzamidine hydrochloride). After centrifugation at 3,000×g for 5 min, supernatants were precipitated with a 3× volume of 1.3% potassium acetate in absolute ethanol at −20° C. for 2 h and the precipitation was isolated with centrifugation at 14,000×g for 20 min. The ethanol precipitation was repeated twice, and the final precipitation was used for measurement of proteoglycans. The accumulation of proteoglycan within the sponges was evaluated in an ELISA with anti-keratan sulfate, anti-chondroitin 4-sulfate, and anti-chondroitin monoclonal antibodies. The ethanol precipitates were dissolved in carbonate buffer (35 mM NaHCO$_3$, 18 mM Na$_2$CO$_3$, pH 9.8) and re-precipitated in the same manner. Dilutions of the samples were subjected to immunochemical analysis. A proteoglycan monomer from bovine nasal cartilage (ICN Biomedicals) was used as a standard. Fifty-microliter aliquots of each sample or standard were coated onto 96-well plates overnight at 4° C., rinsed, and digested for 1 h at 37° C. with 50 μl of 0.1 units/ml protease-free chondroitinase ABC (Seikagaku America, Falmouth, Mass.) in 0.1 M Tris-HCl and 0.03 M sodium acetate (pH 8.0). Each well was treated with 200 μl of blocking solution (BLOTTO, Pierce, Rockford, Ill.). After digestion with chondroitinase ABC digestion, antibodies to chondroitin Di-4 sulfate proteoglycan (Clone; 2-B-6, Seikagaku America) was used at a 1:3000 dilution in PBS (pH 7.4) and incubated for 2 h at room temperature. The second antibody, goat anti-mouse IgG+IgM-biotin conjugate (Pierce), was used at a 1:20,000 dilution in PBS and incubated for 1 h. For enhancement, a phosphatase-streptavidin conjugate (GIBCO/BRL Laboratory) was added at 1:1000 dilution with PBS for 1 h. Between steps, the wells were rinsed with 0.05% Tween 20-PBS. Each well was incubated with 100 μl of 4 mg/ml p-nitrophenylphosphate (GIBCO/BRL Laboratory) in a buffer containing 22 mM sodium carbonate, 28 mM sodium bicarbonate, and 1 mM $MgCl_2$ (pH 9.8) for 1 h. Each reaction was terminated by the addition of 100 μl of 1N NaOH. The optical density at 405 nm was measured with a microtiter plate reader (Bio-Rad, Cambridge, Mass.).

Western blotting. For biochemical measurement of matrix components, the samples were homogenized with a pistol homogenizer for 5 sec at 4° C. Homogenates were placed on ice for 15 min and then centrifuged at 3,000 rpm for 5 min at 4° C. Each of eight replicate samples was extracted for 48 h at 4° C. in 1 ml of 4 M guanidine hydrochloride, 10 mM EDTA (pH 5.8), with protease inhibitors (0.1 M ε-aminohexanoic acid and 0.005 M benzamidine hydrochloride). Mizuno S et al. (1996) *Exp Cell Res* 227:89-97. After centrifugation at 3,000×g for 5 min, supernatants were precipitated with a 3× volume of 1.3% potassium acetate in absolute ethanol at −20° C. for 2 h and the precipitation was isolated with centrifugation at 14,000×g for 20 min. The ethanol precipitation was repeated twice, and the final precipitation was used for measurement of proteoglycans. The accumulation of proteoglycan within the gel was evaluated with anti-chondroitin 4-sulfate monoclonal antibody.

Aliquots of each sample (20 μl) were subjected to electrophoresis with an SDS-PAGE gel (Invitrogen). After electrophoresis at 150 mV, each gel was transferred to a PVLA membrane (Pharmacia) at 25 mV for 45 min. The membrane was blocked with Tween-20 PBS with 5% non-fat dried milk, overnight at room temperature. The membrane was incubated in primary antibody for overnight at 4° C. The membrane was washed with Tween 20-PBS, 3 times for 5 min. For detection by chemiluminescence, protein blots were placed protein side up onto polyvinylidene chloride wrap, the blots were applied with detection reagent followed by manufacturer's instruction (ECL plus Western blotting detection system, Amersham, Buckinghamshire, England). A sheet of radiographic film (Heyperfilm ECL, Amersham) was placed on top of the wrapped membrane with polyvinylidene chloride wrap, exposed for 1 min, and developed.

Preliminary data from porcine articular chondrocytes using collagen gel/sponge showed that static culture condition after HFP application promoted more S-GAG accumulation than HFP alone. HFP has the potential to stimulate chondrocyte specific metabolic function, e.g., highly sulfated chondroitin sulfate production. Meanwhile, cellular and material properties of the cell construct also need to be considered as a result of proliferation and newly accumulated ECM. These biological changes (growth) influence the material properties, e.g., permeability of nutrient and gas, of the construct. A static culture condition promotes stabilization of ECM and embedding cells. The semi-permeable membrane pouch plays the role of a partition between the cell/carrier and medium phase when the cells are seeded. Thus ECM accumulation occurs even at the beginning of culture. As it turns out, the majority of proliferated cells (PCNA-positive cells) was seen on the surface of a construct. Using a semi-permeable membrane pouch, there is no interface between cell/construct substrate and medium flow.

Cell attachment to substrate may be required for cell proliferation. In this case, fibrotic collagen fragments are optionally added to supplement the amorphous carrier. If cell adhesion to substrate is essential, the substrate is optionally coated with arginine-glycine-aspartic acid (RGD)-peptide (Integra, Calif.) or another adhesion molecule.

Proliferation and chondrogenic phenotypes are stimulated with an optimal HFP algorithm, which is designed using markers of cartilage-specific ECM.

Example 5

Evaluation of Chondrogenic Activity in the Amorphous Carrier Within a Semi-Permeable Membrane at Pre-Selected Magnitude of Hydrostatic Pressure and Determination of an Algorithm for Hydrostatic Pressure This example examines chondrogenic activity (cell viability, proliferation, phenotypes) in the amorphous carrier within a semi-permeable membrane at pre-selected magnitude of hydrostatic pressure and determines an algorithm for hydrostatic pressure. The molecular weight of the newly synthesized ECM (mainly chondrocyte-specific proteoglycan, or aggrecan), is $2\text{-}3\times10^3$ kDa. Type II collagen fibers are 500 nm in length. The ECM is maintained within a semi-permeable membrane pouch. Chondrocytes are embedded within their newly synthesized ECM, and carrier materials are chosen that are efficiently kept in the pouch (defined cut-off size from Example 2). By manipulating physical stimuli (hydrostatic fluid pressure and its algorithms with static condition; medium flow rate), cellular activity (cell viability and proliferation as well as phenotypic expression) is altered. Under optimal physical stimuli, chondrocytes start the regenerative process in vitro and de novo. This example defines optimal culture conditions using the aforementioned biological markers.

Preliminary histological findings indicated uniform cell distribution and intense ECM accumulation within collagen gel carrier sealed within the membrane. The series of physical stimuli and algorithms, as well as quantitative methods of evaluation, are shown in Table 1. Hydrostatic pressure is applied at constant 0, 0.7, or 3.5 MPa or at cyclic 0.7 or 3.5 MPa at 0.5 Hz. The pouch culture is harvested 1, 3, 7, and 14 days after seeding. In addition to the amorphous carrier, incorporated hyaluronan (800-1200 kDa) is useful to present as a binding site for aggrecan until newly synthesized hyaluronan is available. The methods of histological and biochemical assays (Table 1) are essentially as have been previously described.

Preliminary data indicated that cell proliferation and type II collagen synthesis are stimulated with applied hydrostatic fluid pressure. A static culture period (i.e., ambient pressure) favors accumulation of S-GAG. A target algorithm uses static culture mode for S-GAG accumulation and hydrostatic fluid pressure mode for proliferation.

Example 6

Figure 4:
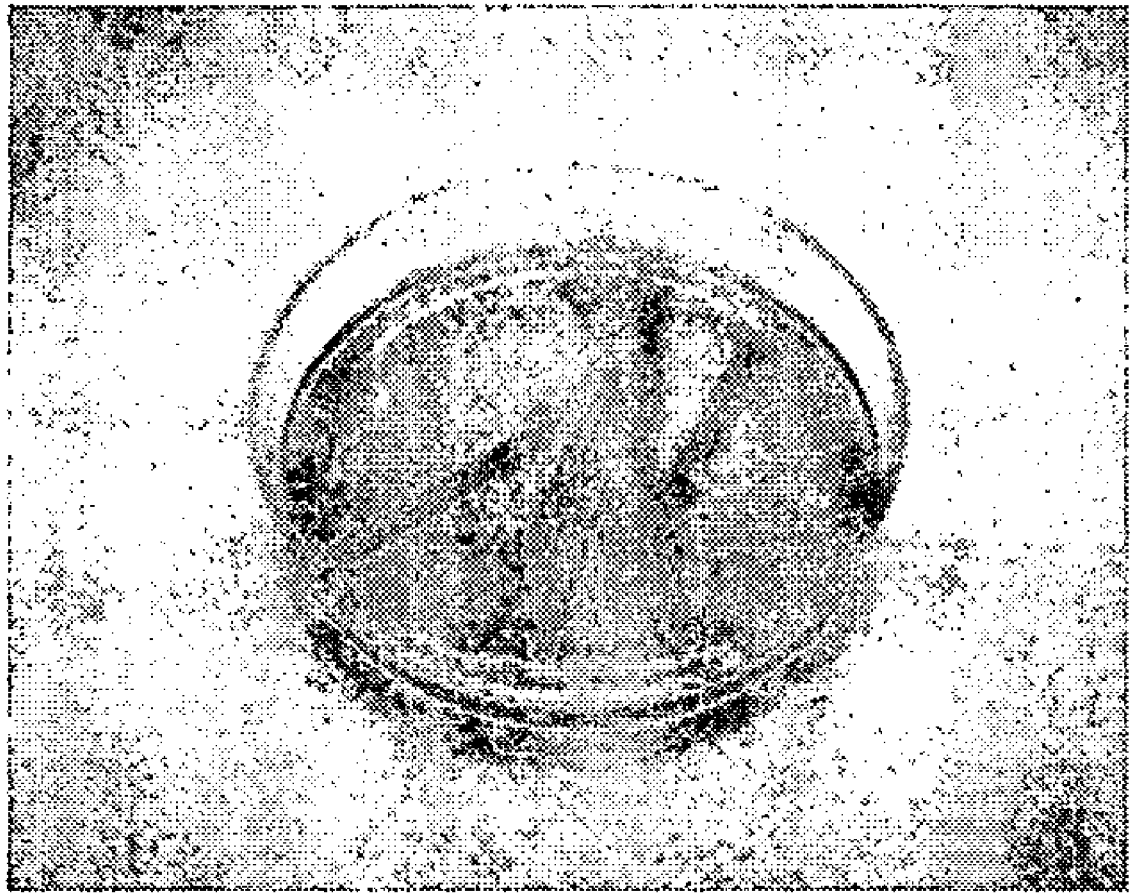
FIG. 4 is a photographic image depicting six semi-permeable membrane pouches, each containing cells/collagen gel carrier, in a dish.

Development of an Injectable Chondrocyte/Matrix Cultured in a Semi-Permeable Membrane Pouch and Manipulated Using Physical Stimuli The core methodology was tested using amorphous cell carriers: 0.3% collagen gel (Cohesion), PEG-based hemostat (COSEAL™, Baxter), and 1.2% calcium-alginate gel (Inotech). Bovine articular chondrocytes were suspended with the carrier and introduced into a semi-permeable membrane pouch (PVDF, 1 mm inside diameter, 1.2 mm outside diameter, MWCO size: 500 kDa). The cell/gel carrier in the pouch was incubated for 1 week at static (ambient) pressure, cyclic hydrostatic fluid pressure at 0.7 MPa, 0.1 Hz for 4 h followed by 20 h rest, or constant hydrostatic pressure at 0.7 MPa for 4 h followed by 20 h rest. Bovine articular chondrocytes in culture produced S-GAG and accumulated matrix in the collagen and alginate gels (FIG. 4).

Figure 5:
FIG. 5 is a series of six photomicrographic images showing significant differences in both cell shape and geometry that were noted among static, constant hydrostatic pressure, and cyclic hydrostatic pressure culture conditions. TB, toluidine blue.
Figure 5:
Figure 5:
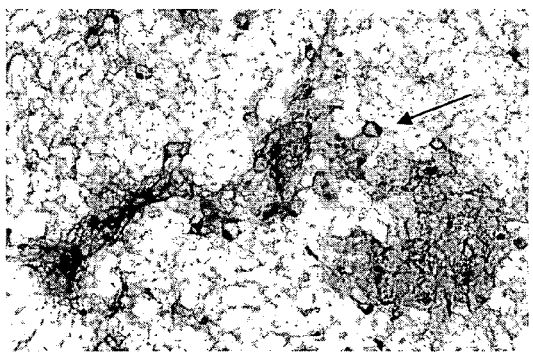
Figure 5:
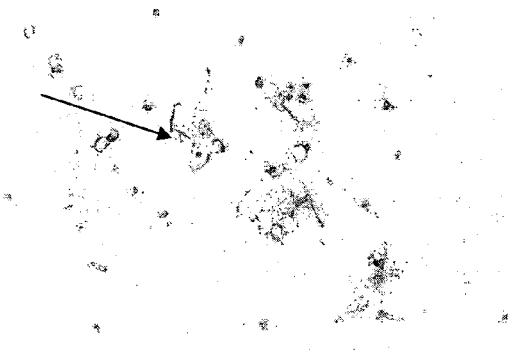
Figure 5:
Figure 5:
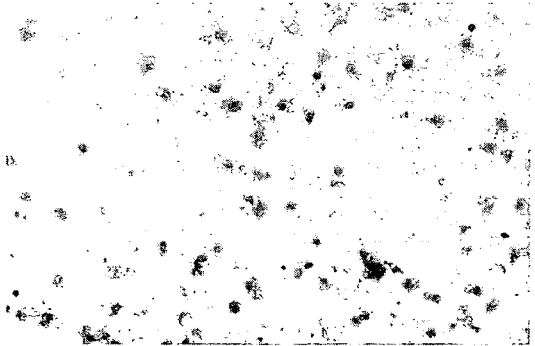

Significant differences in both cell shape and geometry were noted among static, cyclic, and constant hydrostatic pressure conditions (FIG. 5). Under static culture conditions, the predominant metachromatic ECM accumulated, but the filled collagen gel shrank. Under cyclic hydrostatic pressure, fiber-like ECM accumulated. Under constant hydrostatic pressure, the cells had a lacunae-like shape (arrows) and were surrounded by metachromatic ECM and radial fiber-like accumulation.

Example 7

Charge Modification of the Semi-Permeable Membrane Pouch

Preliminary results in Example 3 indicated that infiltration of molecular tracer to native articular cartilage was restricted. The infiltration depended upon pI of fluorescent marker and longitudinal tissue morphology. These data indicate it may be possible to control extracellular matrix (ECM) accumulation. If the chondrocytes successfully produce highly sulfated ECM, the ECM will accumulate within the bag. Charge modification may be used to control selective molecule permeability. For example, the membrane is coated with poly-L-lysine to create a positively charged surface.

With hydrostatic fluid pressure treatment, small molecular weight molecules infiltrate efficiently into the pouch under cyclic hydrostatic fluid pressure. Large molecular weight products, e.g., ECM, are kept inside of the pouch. Biodegradable amorphous polymer is replaced with newly synthesized ECM.

Example 8

Figure 6:
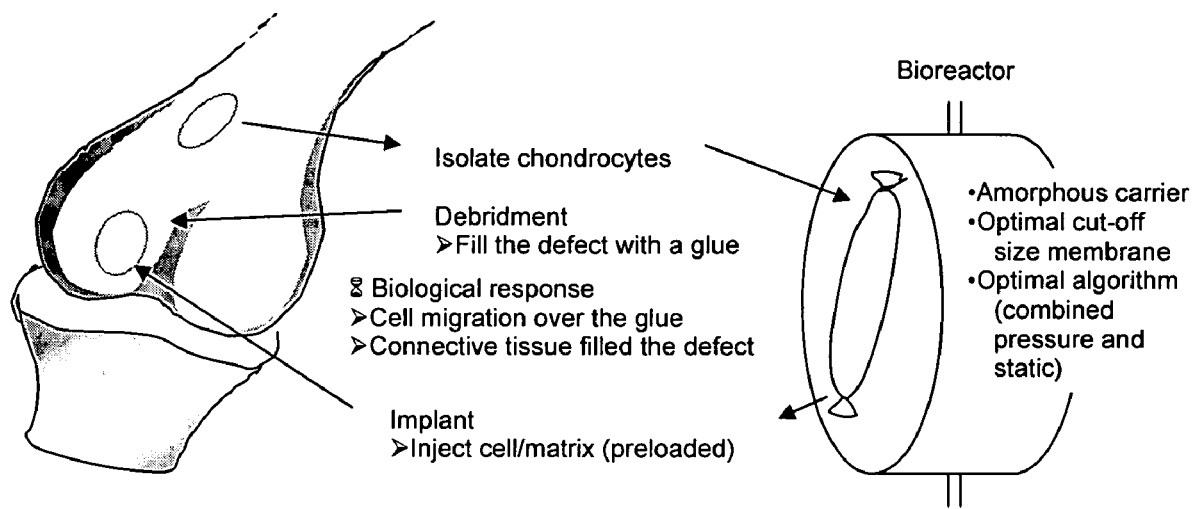
FIG. 6 is a schematic drawing illustrating the method of surgical treatment using injectable chondrocyte/matrix cultured in a semi-permeable membrane pouch and manipulated using physical stimuli.

Surgical Treatment Using Autologous Injectable Chondrocyte/Matrix Cultured in a Semi-Permeable Membrane Pouch and Manipulated Using Physical Stimuli This surgical approach uses injectable cell/matrix and relies upon a self-healing process and in vitro cell treatment instead of total tissue replacement. This repair technique uses the tissue's own resurfacing ability to make a surface layer of cartilage at the site of injury. Once the surface layer is formed with migrated cells, chondrocyte cells (with their own matrix) are injected under the new surface and the defect filled. This surgical approach permits use of arthroscopy instead of more invasive surgical methods. Based on optimized culture methods developed using methods of Examples 1-7, injectable cell/matrix treated with physical stimuli facilitates regeneration of cartilage de novo. To form a cell/matrix construct in vitro, a series of in vitro culture methodologies are developed by implementing use of a semi-permeable membrane pouch for efficient ECM accumulation, selecting an amorphous cell carrier, and defining an algorithm of physical stimuli (FIG. 6). This procedure incorporates the following three steps:

1) Isolate chondrocytes, clean the damaged defect, and fill the defect with fibrin glue.
2) Expand isolated cells and incubate with an amorphous gel within a semi-permeable membrane pouch at optimal physical stimuli in culture using the bioreactor of Example 1.
3) Inject the cell/matrix in between the new cover of surface layer or superficial transitional zone of cartilage and subchondral bone.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages of the invention are not necessarily encompassed by each embodiment of the invention.

All references, patents and patent publications that are recited in this application are incorporated in their entirety herein by reference.

I claim:

1. A method of culturing cells in vitro, comprising
   contacting a population of cells selected for in vitro culture with a biodegradable amorphous carrier;
   placing the contacted population of cells in a cell space for receiving the cells, said cell space being bounded at least in part by a semi-permeable membrane having a molecular weight cut-off greater than 100 kDa and up to 1,000 kDa; and
   periodically applying pressure to the contacted population of cells.

2. The method of claim 1, wherein the cells comprise chondrocytes and, optionally, precursor cells thereof.

3. The method of claim 1, wherein the cells consist essentially of chondrocytes.

4. The method of claim 1, wherein the biodegradable amorphous carrier comprises type I collagen.

5. The method of claim 1, wherein the biodegradable amorphous carrier comprises a hydrogel chosen from dextran, chondroitin sulfate, polyethylene glycol, hyaluronan, and any combination thereof.

6. The method of claim 1, wherein the cell space for receiving the cells consists of a semi-permeable membrane tube comprising at least one closable opening for receiving the cells.

7. The method of claim 1, wherein the cell space for receiving the cells consists of a semi-permeable membrane pouch comprising a closable opening for receiving the cells.

8. The method of claim 1, wherein the semi-permeable membrane has a molecular weight cut-off of at least 200 kDa.

9. The method of claim 1, wherein the semi-permeable membrane has a molecular weight cut-off of at least 250 kDa.

10. The method of claim 1, wherein the semi-permeable membrane has a molecular weight cut-off of at least 500 kDa.

11. The method of claim 1, wherein the semi-permeable membrane has a molecular weight cut-off of 1,000 kDa.

12. The method of claim 1, wherein the semi-permeable membrane is a Semi-permeable membrane carrying a net positive charge.

13. The method of claim 12, wherein the semi-permeable membrane carrying the net positive charge is a semi-permeable membrane coated with poly-L-lysine.

14. The method of claim 1, wherein the periodically applying pressure comprises applying 0.5 to 3.5 MPa at 0.001 to 1 Hz.

* * * * *

UNITED STATES PATENT AND TRADEMARK OFFICE
CERTIFICATE OF CORRECTION

PATENT NO. : 7,462,484 B2
APPLICATION NO. : 11/194040
DATED : December 9, 2008
INVENTOR(S) : Shuichi Mizuno It is certified that error appears in the above-identified patent and that said Letters Patent is hereby corrected as shown below:

At column 29, claim 12, line 7, "Semi-permeable" should read --semi-permeable--.

At column 30, claim 14, line 5, "0.00 1" should read --0.001--.

Signed and Sealed this

Tenth Day of February, 2009

JOHN DOLL
*Acting Director of the United States Patent and Trademark Office*